United States Patent [19]

Orlando et al.

[11] Patent Number: 5,189,056

[45] Date of Patent: Feb. 23, 1993

[54] PROTECTION OF MOIST STRATIFIED SQUAMOUS EPITHELIA AGAINST DAMAGE FROM NOXIOUS LUMINAL AGENTS

[75] Inventors: Roy C. Orlando, Chapel Hill; Nelia A. Tobey, Raleigh, both of N.C.

[73] Assignee: University of North Carolina at Chapel Hill, Chapel Hill, N.C.

[21] Appl. No.: 452,393

[22] Filed: Dec. 19, 1989

[51] Int. Cl.$^5$ .................... A61K 31/10; A61K 31/385
[52] U.S. Cl. .................................... 514/439; 514/522; 514/554; 514/646; 514/709; 514/925; 514/711
[58] Field of Search ............... 514/439, 709, 522, 554, 514/646, 711

[56] References Cited

U.S. PATENT DOCUMENTS 3,886,285  5/1975  Bentley et al. .................. 514/709 X
4,891,356  1/1990  Szabo ............................. 514/709 X

OTHER PUBLICATIONS

Annals of Internal Medicine, 1982; 97: pp. 93-103; "Gastroesphageal Ruflux", Pathogenesis, Diagnosis and Therapy, by Joel E. Richter, M.D.; and Donald O. Castell M.D.; Bethesda, Maryland.

Digestive Disease, vol. 21, No. 11 (Nov. 1976) pp. 953-956; "Symptomatic Gastroesophageal Reflux: Incidence and Precipitating Factors"; by LCDR Otto T. Nebel, MC, USNR, CDR Michael F. Fornes, MC, USN and CAPT Donald O. Castsell, MC, USN.

J. Clin. Invest. The American Society for Clinical Investigation, Inc. vol. 68, Jul. 1981, pp. 286-293 "Pathophysiology of Acute Acid Injury in Rabbit Esophageal Epithelium", by: Roy C. Orlando, Don W. Powell, and Charles N. Carney, Department of Medicine and Pathology, University of North Carolina School of Medicine.

The American Physiological Society, 0193-1857/1984; "Mechanisms of $H_+$ injury in rabbit esophageal epithelium"; By Roy C. Orlando, Judy C. Bryson, and Don W. Powell; Department of Medicine, University of North Carolina School of Medicine.

The American Gastroenterological Association, 1989;96:1466-1477; "Serosal Bicarbonate Protects Against Acid Injury to Rabbit Esophagus", By: N. A. Tobey, D. W. Powell, V. J. Schreiner, and R. C. Orlando; Department of Medicine, University of North Carolina School of Medicine.

A512 Abstracts of Papers, 1989, Gastroenterology vol. 96, No. 5, Part 2.

Gastroenterology 1991;101:1220-1228; "Mechanisms of Acid Injury to Rabbit Esophaegeal Epithelium" Role of Basolateral Cell Membrane Acidification; By: Nelia A. Tobey and Roy C. Orlando; Department of Medicine, University of North Carolina School of Medicine.

Gastroenterology 1987;93:352-61; "Mucosal Protection by Sucralfate and Its Components in Acid-Exposed Rabbit Esophagus", By: Roy C. Orlando, Nabila A. Turjman, Nella A. Tobey, Virginia J. Schreiner, and Don W. Powell; Department of Medicine, University of North Carolina School of Medicine.

(List continued on next page.)

Primary Examiner—Leonard Schenkman
Attorney, Agent, or Firm—Cushman, Darby & Cushman

[57] ABSTRACT

The present invention is related to the protection of moist stratified squamous epithelia against damage from exposure to noxious luminal agents. Protection of moist stratified squamous epithelia against these noxious luminal agents is afforded by chemical compounds having one of the following reactive groups in their molecule: $X—SO_3^-$, where X represents oxygen or carbon, and $XO_4^=$ or $X_2O_7^=$, where X represents an element from group VIb or sulfur of group VIa of the periodic table. Compounds that provide protection against injury to moist stratified squamous epithelia that illustrate the protective characteristic of these reactive species are the sulfonates, the sulfate esters and the tetrahedral-shaped divalent oxy-anions of the transition metals in group VIb or of sulfur. The reason for protection by these compounds is that they stabilize the intercellular junctions of moist stratified squamous epithelia so as to prevent the increase in permeability across the junctions that normally accompanies exposure to noxious luminal agents like HCl or N-acetylcysteine.

5 Claims, 17 Drawing Sheets

OTHER PUBLICATIONS

Rapid Communications by the American Physiological Society, 1986; pp. G866–G869; "Cytoprotective effect of sulfate ions in acid–exposed rabbit esophagus", By: Nelia A. Tobey, Roy C. Orlando, Virginia J. Schreiner, and Don W. Powell; Department of Medicine, University of North Carolina School of Medicine.

Abstracts of Papers, 1986; Gastroenterology vol. 90, No. 5, Part 2, p. 1668.

Abstracts of Papers, A461, May 1988; Gastroenterology vol. 94.

Biochimica et Biophysica Acta, 978 (1989) pp. 249–256, BBA 74301; "Anion transport through the contraluminal cell membrane of renal proximal tubule. The influence of hydrophobicity and molecular charge distribution on the inhibitory activity of organic anions", By: Gunter Fritzsch, Gerhard Rumrich and Karl Julius Ulrich.

Plugers Archive, European Journal of Physiology, Springer–Verlag 1985, pp. 293–299; "Contraluminal sulfate transport in the proximal tubule of the rat kidney", By: K. J. Ullrich, G. Rumrich, and S. Kloss.

J. Physiol (1986). 379, pp. 367–376; "Sulphate Transport Into Vesicles Prepared From Human Placental Brush Border Membranes: Inhibition By Trace Element Oxides", By: C. A. R. Boyd and D. B. Shennan; From the Department of Human Anatomy, University of Oxford.

A Simple Method for the Isolation and Purification of Total Lipides From Animal Tissues, By: Jordi Folch, M. Lees, and G. H. Sloane Stanley; (From the McLean Hospital Research Laboratories, Waverley, and the Department of Biological Chemistry, Harvard Medical School, Boston Massachusetts), pp. 497–509. (1956).

Chem. Pharm. Bull 361(2) No. 2, 1988, pp. 641–657; "Synthesis and Anti–ulcer Activities of Sodium Alkylazulene Sulfonates"; By: Takashi Yanagishawa, Shuichi Wakabayashi, Tsuyoshi Tomiyama, Masafumi Yasunami and Kahei Takase.

Biochemicals Organic Compounds, Diagnostic Reagents; Alphabetical List of Compounds, p. 933; #S-6381, Sigma Chemical.

Budesinsky, B. Analytical Chemistry 37:1159, 1965; Modification of Flask Method of Sulfur Determination "Determination of Sulfates with Sulfonazo III".

Z. Anal Chem., Bd. 210, pp. 161–166, 1965; "Complexes of Metallochromic Substances. VII Spectrophotometric Determination of Barium and Sulphates by Means of Sulphonazo III"; By B. Budesinsky and D. Vrzalova.

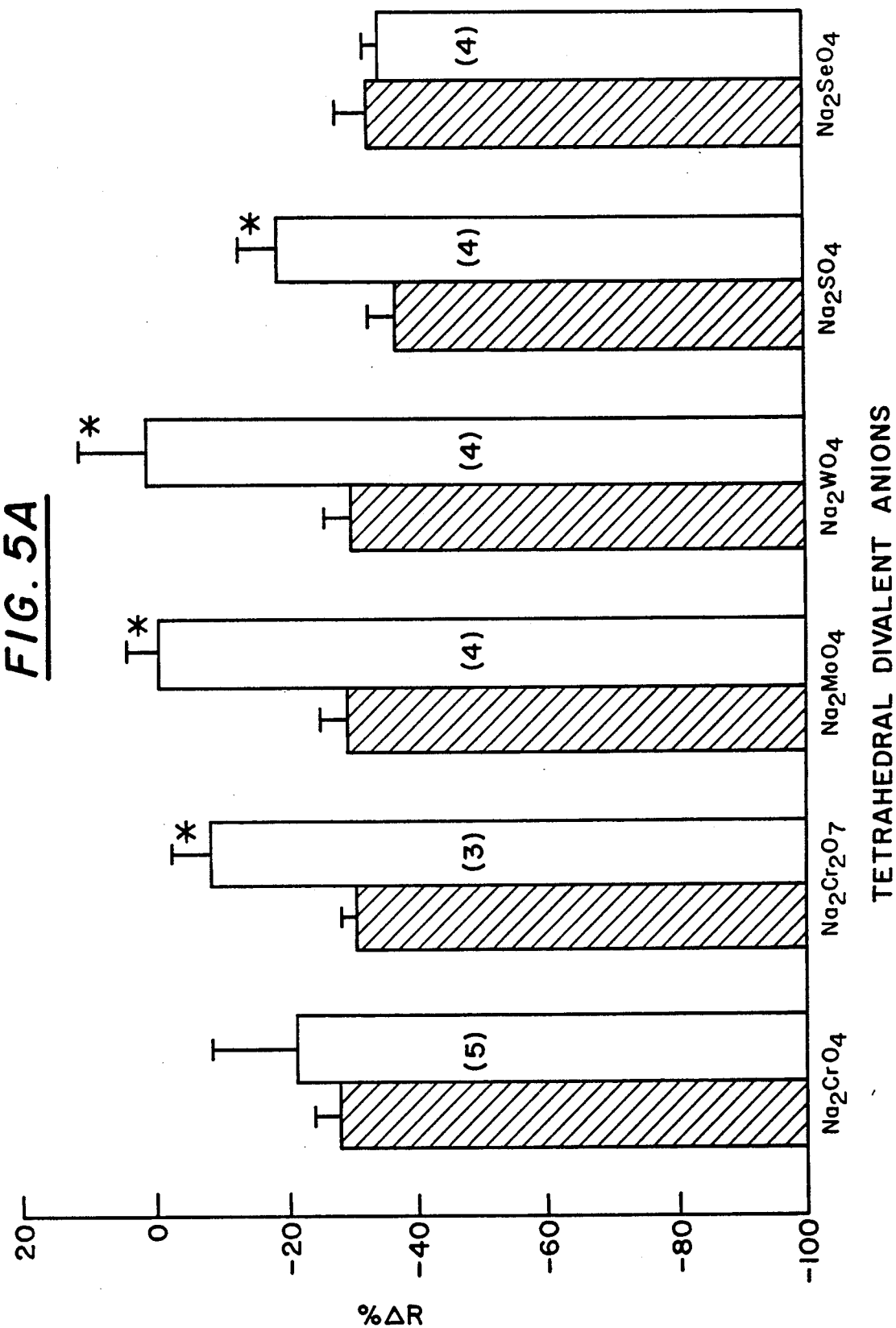

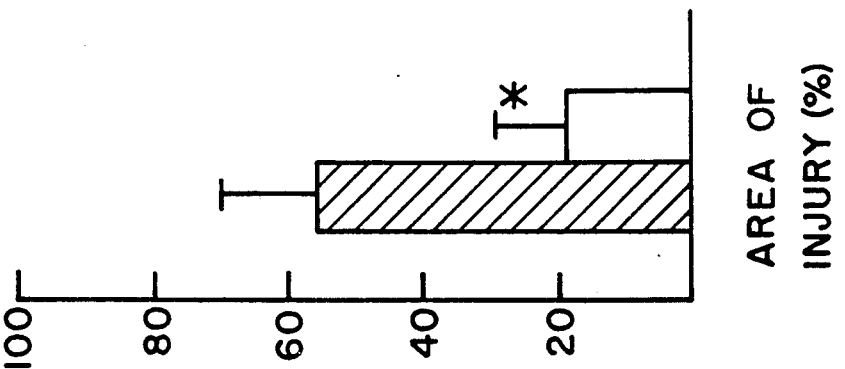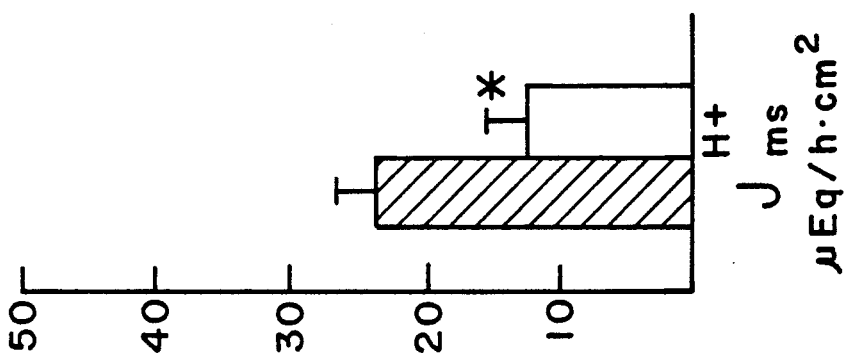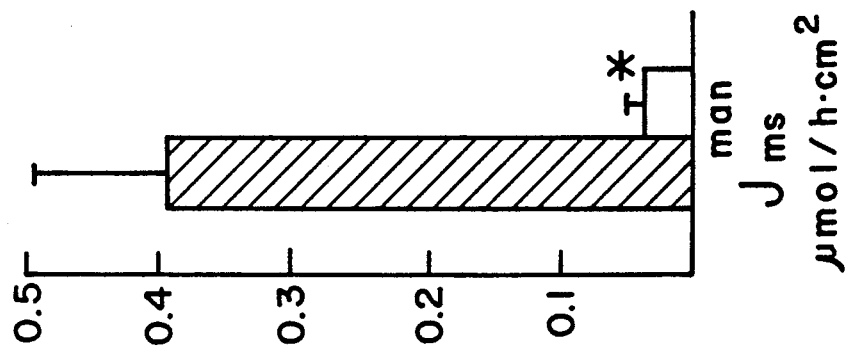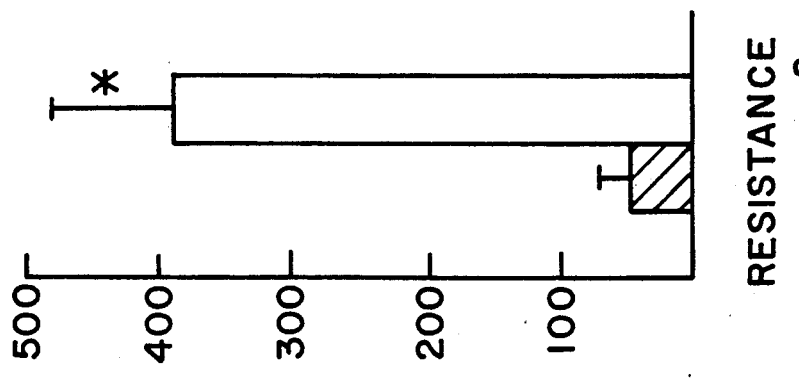

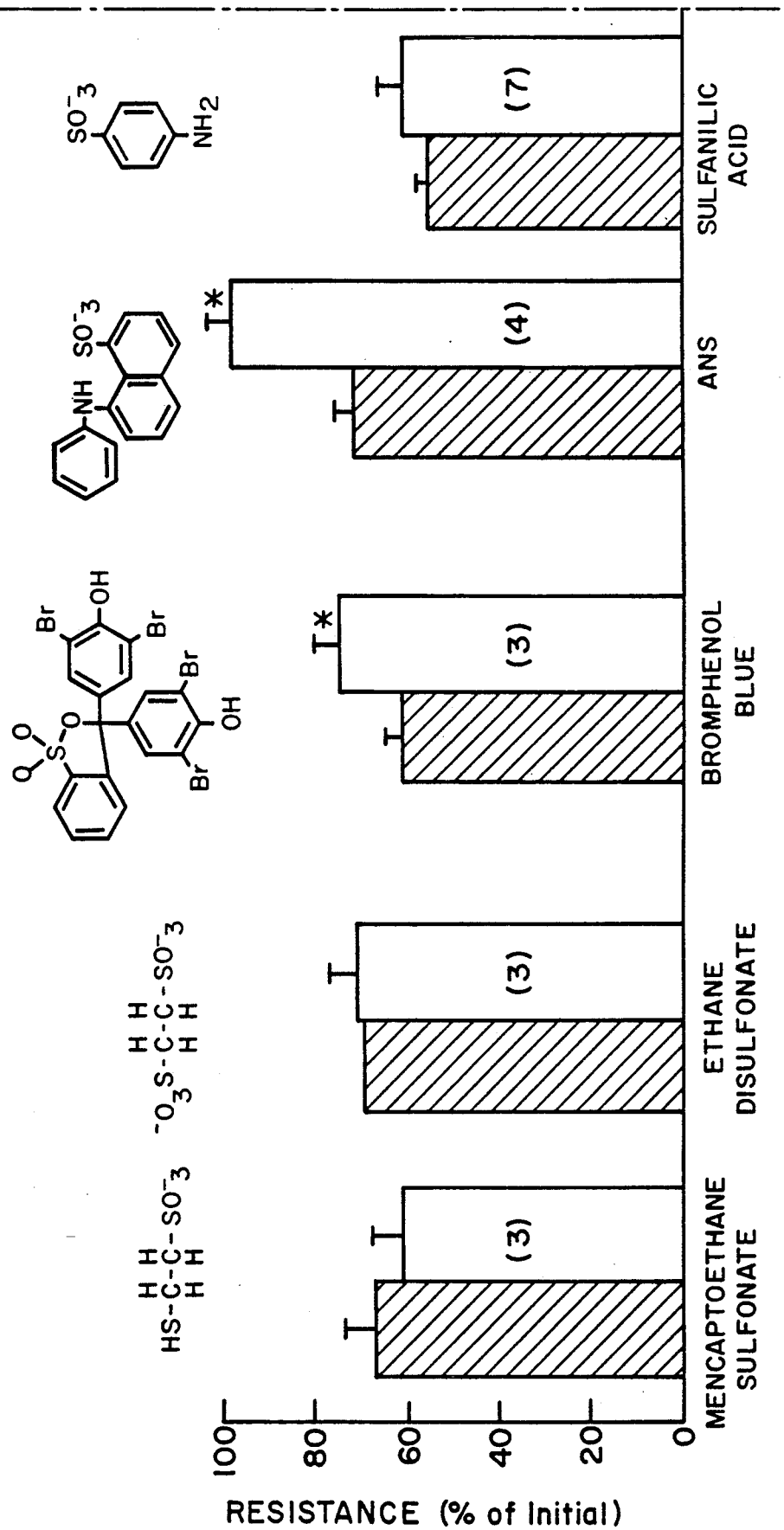

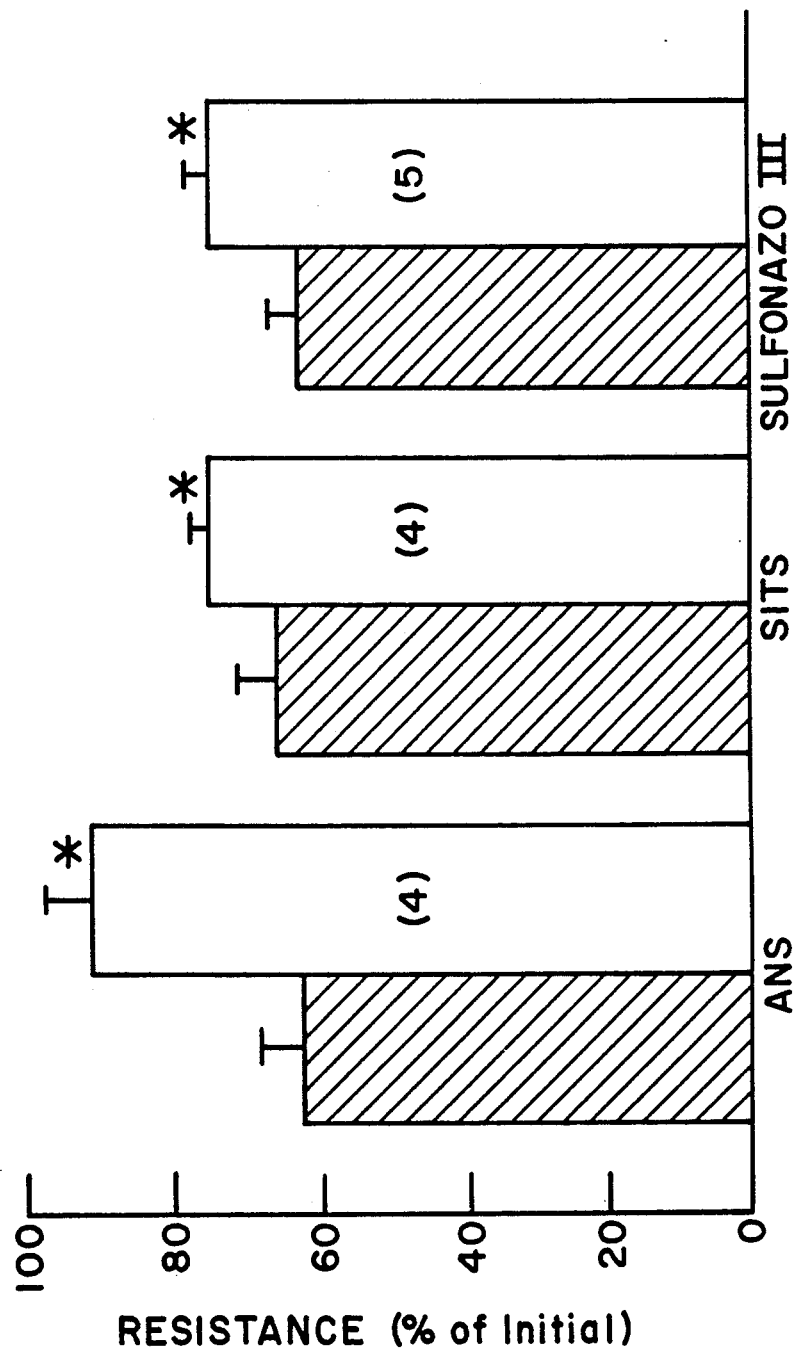

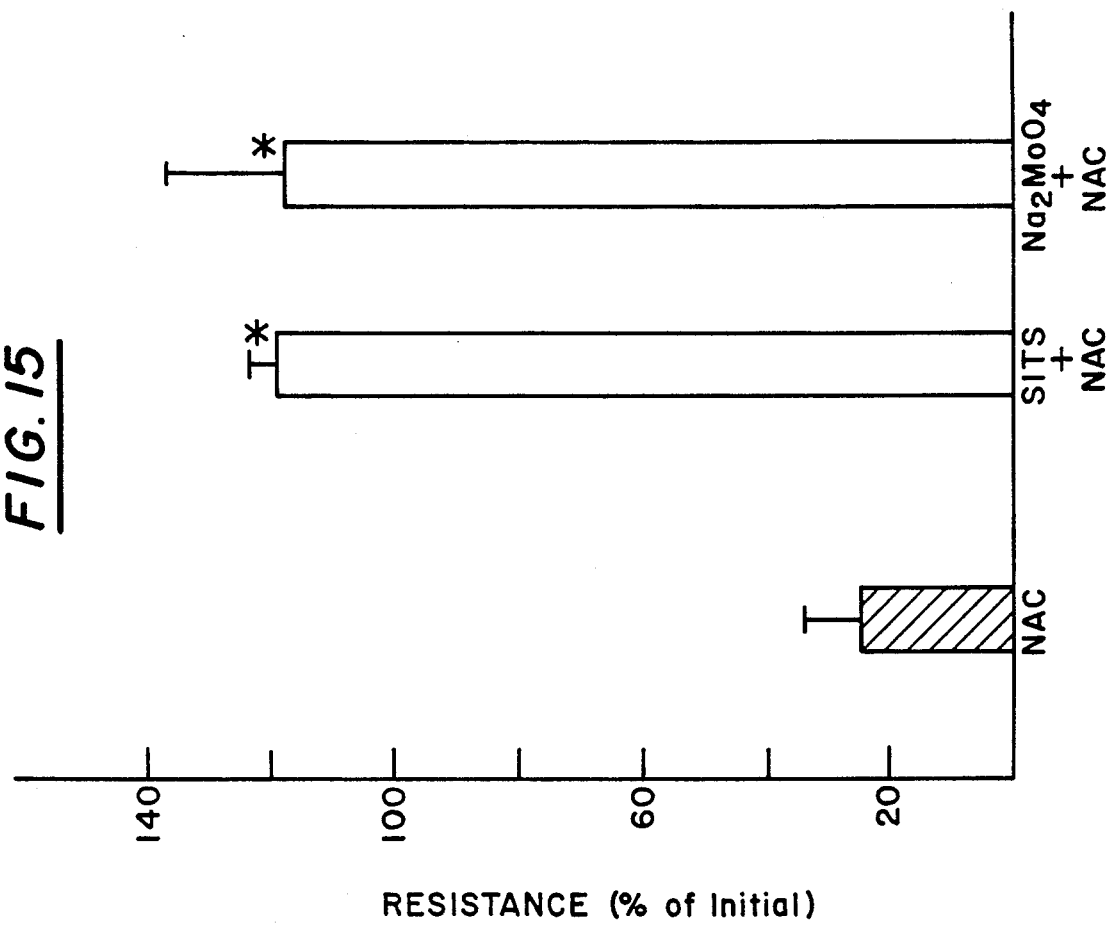

PROTECTION OF MOIST STRATIFIED SQUAMOUS EPITHELIA AGAINST DAMAGE FROM NOXIOUS LUMINAL AGENTS

BACKGROUND OF THE INVENTION

1. Field of the Invention

This invention, in general, relates to a method for protecting moist stratified squamous epithelia against damage from exposure to noxious luminal substances.

In particular, this invention relates to:

I) the identification of a mechanism for protecting moist stratified squamous epithelia against damage from exposure to luminal substances such as hydrochloric acid (HCl) and N-acetylcysteine. This is based on the recognition that some of the noxious effects of luminal substances on moist stratified squamous epithelia are a consequence of their ability to increase the permeability across the intercellular junctions (paracellular pathway), and that moist stratified squamous epithelia can be protected from the noxious effect of luminal exposure to these substances by stabilizing their intercellular junctions so as to block the increase in permeability through this route; and II) the identification of 3 chemical reactive groups and three classes of chemical compounds derived from them that provide protection to moist stratified squamous epithelia against damage from luminal HCl or N-acetylcysteine by stabilizing their intercellular junctions so as to block the increase in paracellular permeability that normally accompanies such exposure.

More specifically this invention relates to:

A) the identification of a new mechanism for protection of esophageal epithelia against acid injury and that is by stabilizing their intercellular junctions so as to block the increase in paracellular permeability that occurs with exposure to luminal acid; the ability to protect by preventing the increase in paracellular permeability represents a new mechanism of "cytoprotection", cytoprotection by definition meaning a method of protecting against acid injury to tissue without inhibiting gastric acid secretion or altering luminal acidity, B) the identification that the mechanism described in (A) also applies to protection of esophageal epithelia against damage from luminal N-acetylcysteine and other noxious luminal substances that primarily damage by increasing permeability through the paracellular pathway, C) the identification that the mechanism described in (A) also applies to protection of buccal and other moist stratified squamous epithelia against damage from luminal HCl, D) the identification of three chemical reactive groups and three classes of chemical compounds derived from them that with topical application protect esophageal epithelia against damage from luminal HCl by stabilizing their intercellular junctions so as to block the HCl-induced increase in paracellular permeability. The three reactive groups are:

a) $X\text{-}SO_3^-$, where X represents an oxygen or carbon linkage covalently or ionically bound to an organic or inorganic molecule, and the tetrahedral-shaped divalent oxy-anionic groups:

b) $XO_4^=$ and c) $X_2O_7^=$, where X represents an element from group VIb of the periodic table or sulfur from group VIa covalently or ionically bound to an organic or inorganic molecule.

The three classes of chemical compounds derived from them are:

a) the sulfonates, e.g. 4-acetamido-4'-isothiocyano-2,2'-stilbene disulfonate (SITS), 8-anilino-naphthalene-1-sulfonate (ANS), dinitrodisulfonic acid stilbene (DNDS), sulfonazo III, 4,4'-diisothiocyano-2,2'-stilbene disulfonate (DIDS), bromphenol blue, b) the sulfate esters, e.g. sucrose octasulfate, dextran sulfate, and c) the tetrahedral-shaped divalent oxy-anions, e.g. sodium chromate, sodium dichromate, sodium molybdate, sodium tungstate, sodium sulfate, E) the identification that the reactive groups and classes of compounds referred to in (D) also protect esophageal epithelia against damage from luminal N-acetylcysteine and other luminal agents that damage by increasing paracellular permeability, F) the identification that the reactive groups and classes of compounds referred to in (D) also protect buccal epithelia against damage from exposure to HCl and other luminal agents that damage by increasing paracellular permeability, G) the identification that the reactive groups and classes of compounds referred to in (D), if shown to be non-toxic to humans, can be used orally as a treatment to prevent reflux esophagitis or its symptoms (e.g., heartburn), H) the establishment of a technique using the Ussing chamber and voltage clamp for identifying agents capable of protecting esophageal, buccal and other moist stratified squamous epithelia against luminal HCl, N-acetylcysteine and other noxious luminal agents that damage by increasing the permeability through the paracellular pathway.

2. Background Information

Reflux esophagitis is a chronic disease that results from repeated and prolonged contact of esophageal epithelium with gastric acid (Richter J. E., Castell DO. Gastroesophageal Reflux: Pathogenesis, Diagnosis, and Therapy. Ann Intern Med 1982; 97–103). This represents one of the most common illnesses in humans as attested to by the fact that there is almost universal appreciation of its characteristic symptom, "heartburn". It has been reported that 7% of the U.S. population experience heartburn on a daily basis and that 36% experience it at least once per month (Nebel TO, Fornes MF, Castell DO: Symptomatic gastroesophageal reflux: Incidence and precipitating factors. Am J Dig Dis 1976; 21:953). In general terms reflux esophagitis and its major symptom, heartburn, develop as a result of the chemical damaging effects of gastric acid on the esophageal epithelium, and progression of this damaging action can lead to esophageal ulceration with bleeding, esophageal obstruction due to stricture formation and the development of a Barrett's esophagus (i.e. replacement of the squamous epithelial lining by a metaplastic columnar epithelium), the latter a premalignant lesion. For these reasons reflux esophagitis is a serious disease.

There are two general approaches to treatment of reflux esophagitis. The first and thus far most successful is to reduce gastric acidity. This is usually accomplished by inhibiting HCl secretion with either agents like cimetidine that block the parietal cell $H_2$-receptor or with agents like omeprazole that block the parietal cell enzyme H-K ATPase. Although the former have been only moderately successful, the latter which have recently been marketed reportedly heal up to 95% of patients with reflux disease. However the relapse rates when therapy is stopped are high for both types of agents, and that for omeprazole is 80% within six months of stopping therapy. Further although patients may respond to retreatment or be prevented from relapse by continuing the drug, there is concern about the safety of omeprazole when used long term. This is because rats treated with omeprazole for long periods have developed gastric carcinoid tumors and these are believed to be secondary to the rebound hypergastrinemia associated with potent acid suppression. For this reason there remains a need for therapeutic agents that can prevent relapse of reflux symptoms and esophagitis following treatment with the more potent acid-suppressing agents.

The second approach to treating reflux esophagitis involves using agents that enhance one of the intrinsic defenses of the esophagus. For example bethanecol and metoclopromide have been used because of their abilities to increase the contractility of the lower esophageal sphincter (LES). This may theoretically be beneficial because the LES is the major barrier to reflux in humans. In practice however these agents have not been very effective.

Another defense mechanism that may be enhanced is that of the tissue's intrinsic resistance to acid digestion, and agents that increase "tissue resistance" without inhibiting gastric acid secretion or luminal buffering have been referred to as "cytoprotective". The inventors' laboratory has been interested in identifying compounds that protect esophagus against acid damage by a cytoprotective action on the epithelium. Such agents, the inventors found, can be identified in vitro by mounting esophageal epithelia in Ussing chambers hooked to voltage clamps and showing that an agent prevents the reduction in the tissue's electrical resistance (R) upon exposure to luminal HCl. The ability of an agent to block the HCl-induced decline in R confers protection on esophageal epithelia because the inventors had previously shown that the HCl-induced decline in R, reflecting an increase in tissue permeability through the intercellular junctions (paracellular pathway), precedes the development of cell necrosis (Orlando, R. C., D. W. Powell, and C. N. Carney. Pathophysiology of acute acid injury in rabbit esophageal epithelium. J. Clin. Invest, 68:286–293, 1981 and Orlando, R. C., J. C. Bryson, and D. W. Powell. Mechanisms of H injury in rabbit esophageal epithelium. Am J. Physiol, 246(Gastrointest. Liver Physiol. 9): G718–G724, 1984). Additional work by the inventors indicates that cell necrosis occurs after the increase in paracellular permeability because it is the latter that allows hydrogen ions to enter the epithelium at a sufficient rate to overcome intercellular buffering by serosal bicarbonate (Tobey, N. A., D. W. Powell, V. J. Schreiner and R. C. Orlando. Serosal bicarbonate protects against acid injury to rabbit esophagus. Gastroenterology 96:1466-77, 1989). The inability to buffer the increased amounts of hydrogen ions eventually leads to cell death by acidifying the region adjacent to the basolateral cell membrane, the basolateral cell membrane unlike the apical cell membrane being unable to tolerate even modest lowering of bathing solution pH without damage to the cell (Tobey NA, Orlando RC. Comparative sensitivity of rabbit esophageal epithelium to serosal versus luminal acid. Gastroenterology 1989; 96:A512).

Sucralfate is a cytoprotective drug developed by Chugai in Japan and marketed in the U.S. by Marion Laboratories. It has been used for treatment of duodenal ulcer in the U.S. and more recently has been studied as a possible treatment for reflux esophagitis in humans (Weiss W., Brunne H., Buttner G. R., et al. Treatment of reflux esophagitis with sucralfate. Dtsch Med Wochenschr 1983; 108:1706). Although the efficacy of sucralfate in humans with reflux esophagitis has not been dramatic, the inventors experiments with sucralfate in esophageal epithelia mounted in Ussing chambers suggested that it contained a potent cytoprotective compound, and that this compound was sucrose octasulfate (Orlando RC, N. A. Turjman, N. A. Tobey, V. J. Schreiner, D. W. Powell. Mucosal protection by sucralfate and its components in acid-exposed rabbit esophagus. Gastroenterology 1987; 93:352–61). Additional experiments also lead the inventors to recognize that the essential component responsible for the cytoprotective property of both sucrose octasulfate and sucralfate was the presence of sulfate ions within the molecules (Tobey, N. A., R. C. Orlando, V. J. Schreiner, D. W. Powell. Cytoprotective effect of sulfate ions in acid-exposed rabbit esophagus. Am J Physiol 1986; 251:G866–869). Also noteworthy was that protection by sucrose octasulfate and sulfate ions in vitro using the Ussing chamber-voltage clamp technique were validated by showing that these same compounds exert protection in vitro in resected specimens from human esophagus (un published observations) and in vivo using as a model the acid-perfused rabbit esophagus (Orlando RC et al. Gastroenterology 1987; 93:352-61 and Tobey NA et al. AM J Physiol 1986; 251:G866–869).

Although the mechanism by which inorganic sulfate ions protected against acid damage to esophageal epithelium was unknown and initially considered to be unique (Tobey NA et al. Am J Physiol 1986; 251:G866–869), a chance occurrence lead us to identify that 4-acetamido-4'-isothiocyano-2,2'-stilbene disulfonate (SITS) also protected Ussing-chambered esophageal epithelium against luminal HCl injury in similar manner and at doses far lower than sulfate ions (Tobey NA, Schreiner V. J., Orlando R. C. Protection by SITS in acid-exposed rabbit esophagus. Gastroenterology 1988; 94:A461). Interestingly the inventors learned from the literature that sulfonates like SITS have a strong affinity for the same membrane receptor as sulfate ions and as such inhibit sulfate transport in rat kidney cells (Fritzsch, G., G. Rumrich, K. J. Ullrich. Anion transport through the contraluminal cell membrane of renal proximal tubule. The influence of hydrophobicity and molecular charge distribution on the inhibitory activity of organic anions. Biochimica et Biophysica Acta 1989; 978:249–256 and K. J. Ullrich, G. Rumrich, S. Kloss. Contraluminal sulfate transport in the proximal tubule of the rat kidney. II Specificity: sulfate-ester, sulfonates and amino sulfonates. Pflugers Arch 1985; 404:293–299). This suggested to the inventors the possibility that sulfonates may protect esophageal epithelia against acid injury by binding to the same receptor in this tissue as sulfate ions. Similar reasoning was applied to the possibility that tetrahedral-shaped divalent oxyanions of elements from group VIb of the periodic table (e.g. chromate) might protect against acid injury to esophageal epithelia when it was learned from the literature that these compounds also bind to sulfate receptors and inhibit sulfate transport in vesicles from placental epithelial cells (Boyd, CAR, D. B. Shennan. Sulphate transport into vesicles prepared from human placental brush border membranes: inhibition by trace element oxides. J Physiol 1986; 379: 367-376). The present invention is based in large part on confirmation of this hypothesis—that is, that binding to a similar site in esophageal epithelium as sulfate ions confers on these additional agents the same protective properties against acid injury observed with sulfate treatment (see summary of invention below). Further the present invention also is broader based in that the protective mechanisms and the identified protective agents also apply to protection of esophageal epithelium against other luminal damaging agents (e.g. N-acetylcysteine) and to protection of other moist stratified squamous epithelia, e.g. buccal epithelium, against injury from luminal HCl.

SUMMARY OF THE INVENTION

Accordingly the present invention relates to:

1) the identification of a general mechanism by which noxious luminal substances like HCl and N-acetylcysteine can be prevented from injuring moist stratified squamous epithelia—that is, by stabilizing the intercellular junctions so as to prevent the increase in paracellular pathway permeability that accompanies exposure to these substances.

2) the identification of three chemical reactive groups and three classes of chemical compounds derived from them that when topically applied protect moist stratified squamous epithelia against damage by stabilizing their intercellular junctions so as to block the increase in paracellular permeability that normally accompanies luminal exposure to noxious substances such as HCl and N-acetylcysteine.

The three reactive groups are:
a) $X-SO_3^-$, where X represents an oxygen or carbon linkage covalently or ionically bound to an organic or inorganic molecule, and the tetrahedral-shaped divalent oxy-anionic groups:
b) $XO_4^=$ and
c) $X_2O_7^=$, where X represents an element from group VIb of the periodic table or sulfur from group VIa covalently or ionically bound to an organic or inorganic molecule.

The three classes of chemical compounds derived from them are:
a) the sulfonates, e.g. 4-acetamido-4'-isothiocyano-2,2'-stilbene disulfonate (SITS), 8-anilino-naphthalene-1-sulfonate (ANS), dinitro-disulfonic acid stilbene (DNDS), sulfonazo III (sodium salt of 3,6-bis-(o-sulfophenylazo)-4,5-dihydroxy 2.7-naphthalenedisulfonic acid), 4,4'-diisothiocyano-2,2'stilbene disulfonic (DIDS), bromphenol blue,
b) the sulfate esters, e.g. sucrose octasulfate, dextran sulfate, and
c) the tetrahedral-shaped divalent oxy-anions, e.g. sodium chromate, sodium dichromate, sodium molybdate, sodium tungstate, sodium sulfate, Furthermore it is the object of the present invention to establish that there is more than one type of injury for which the above reactive groups and protective compounds are capable of providing protection against—e.g. HCl, N-acetylcysteine and others that injure by increasing paracellular permeability, and there is more than one type of moist stratified squamous epithelium that the reactive groups and protective agents are capable of providing protection to—e.g. esophageal epithelium, buccal epithelium and other moist stratified squamous epithelia, e.g. cornea, rumen, vagina, cervix, palate, gingiva, pharynx and tongue.

Moreover it is the object of the present invention to point out that other compounds that have the identified reactive groups or fall into the class of compounds identified above whether currently existing or newly synthesized are likely to be protective, and that since protection extends to HCl-induced injury to esophageal epithelium, may be effective agents for the prevention of reflux symptoms or esophagitis in humans. This latter possibility is particularly true because many of the agents have the following clinically-attractive characteristics: activity at low dose, rapid onset of action, topically active, long duration of action and potential for low toxicity because of poor absorption and lack of effect on baseline permeability and transport by the tissue. Notably these characteristics suggest that many of the agents are likely to be at least as potent and potentially safer than those agents currently used for long term protection against acid damage to esophageal epithelium.

It is another object of the present invention to identify reactive groups and classes of compounds that are more potent than sulfates for providing protection against acid damage to moist stratified squamous epithelia. Furthermore, this invention provides both the structure-activity relationships necessary for either the recognition of other existing agents and/or the synthesis of new compounds with the capacity to protect esophageal and buccal epithelia against acid injury, and the methodology (i.e. Ussing chamber-voltage clamp) to test the agents for protective activity in these tissues.

All publications mentioned are hereby incorporated herein by reference.

BRIEF DESCRIPTION OF THE DRAWINGS

The present invention and many of the attendant advantages thereof are better appreciated by reference to the following detailed description and the accompanying figures and tables.

FIGS. 5A and 5B show that tetrahedral-shaped divalent oxy-anions (38 mM) are capable of protection against acid damage to rabbit esophageal epithelium without being present in the luminal bath at the time of acidification. This was done using a similar experimental design to those of FIG. 1 except that tissues were only transiently exposed (15 min or 1 min) to the agent before acidification of the luminal bath with HCl, (pH 1.6). Notably even after removing the agent, four of the six tetrahedral-shaped divalent oxy-anions were able to protect against the HCl-induced decline in resistance (R).

FIG. 6 shows that protection against the HCl-induced decline in resistance (R) in vitro by a representative tetrahedral-shaped divalent oxy-anion, sodium molybdate ($Na_2MoO_4$), predicted its ability to protect against acid damage to rabbit esophageal epithelium in vivo. In this case rabbit esophagi were cannulated and perfused for 1h with an isotonic solution of HCl (pH 1.0) after an initial 30 min perfusion with either an isotonic molybdate-containing solution or an isotonic saline control solution. Compared to controls, molybdate is shown to be protective to esophageal tissues both morphologically by having a smaller area of injury identified on microscopy and functionally by having lower H+ efflux, lower permeability to mannitol and higher electrical resistance (R). R and mucosal-to-serosal mannitol flux ($J_{man}$ms) were obtained from tissues mounted in Ussing chambers after exposure to HCl in vivo. $J^{H+}$ms, H+ efflux, was measured for the in vivo recirculated HCl solution. Values reported are mean ± SE, n=5.

FIG. 11 shows that like some of the tetrahedral-shaped divalent oxy-anions, brief (1 min) transient luminal exposure to some representative sulfonates (4 mM) can also protect against acid injury to rabbit esophageal epithelium as shown by their ability to prevent the decline in resistance (R) upon subsequent exposure to luminal HCl (pH 1.6) for 1h.

FIG. 15 shows that 38 mM sodium molybdate, a tetrahedral-shaped divalent oxy-anion, or 4 mM 4-acetamido-4'-isothiocyano-2,2'-stilbene disulfonate (SITS), a sulfonate, can not only protect against damage from exposure of rabbit esophageal epithelium to luminal HCl but protects against damage from exposure to luminal N-acetylcysteine, an agent that breaks disulfide bonds. Protection against N-acetylcysteine is shown by the ability of luminal pretreatment with either molybdate or SITS to prevent the decline in electrical resistance (R) of rabbit esophageal epithelium mounted in Ussing chambers and exposed to N-acetylcysteine (6%) for 1 h.

Figure 1:
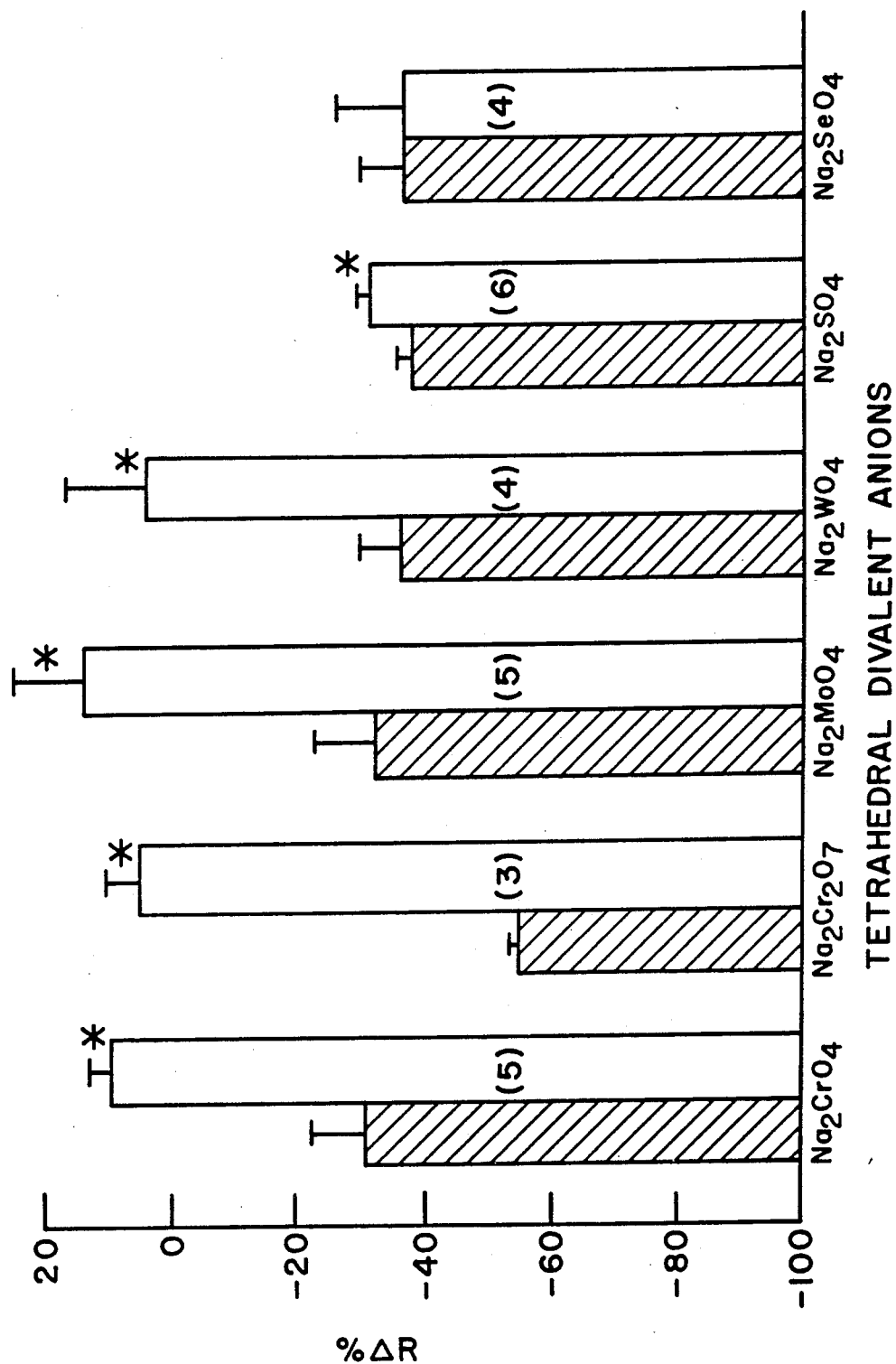
FIG. 1 demonstrates that all of the readily available tetrahedral-shaped divalent oxy-anions containing elements from periodic table VIb and sulfur from VIa provide protection against acid injury to rabbit esophageal epithelium mounted in Ussing chambers. This is illustrated by their ability, when added to the luminal bath, to prevent the decline in tissue resistance (R) upon exposure to high concentrations of luminal HCl (pH 1.6). It is evident from the figure that the tetrahedral-shaped divalent oxy-anions of the transition metals from group VIb have much greater protective effects than sulfate ions. Note: tissues were exposed to equimolar (38 mM) amounts of each agent before acidification of the luminal bath for 1 hour. In these experiments the agent remains in the bath during the acidification period. Also buffering does not account for protection by any agent because the luminal baths were titrated with HCl so that both experimental and control tissues had identical bathing solution pH. The decline in R indicates increasing epithelial permeability due to HCl damage, and thus prevention of the HCl-induced decline in R reflects protection in this system. % Δ R=the 15 percent change from preacidification values. Values are mean ± SE and the number of experiments, n, is shown in parentheses for each agent.
Figure 2B:
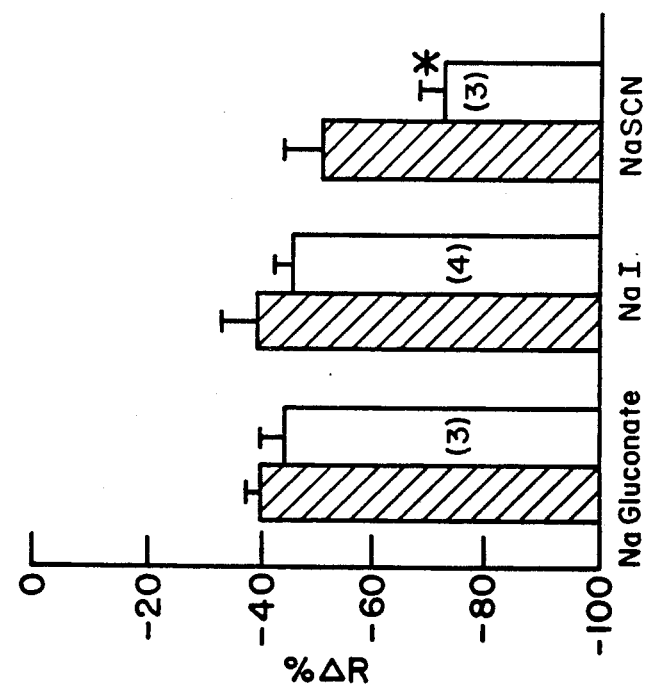
FIG. 2 demonstrates the importance of the tetrahedral shape and divalent oxy-anion state to protection against acid injury to rabbit esophageal epithelium in the Ussing chamber. Using similar methodology as FIG. 1 (i.e. 38 mM of the test agent), the results show that non-tetrahedral shaped divalent oxy-anions or a variety of monovalent anions in the luminal bath fail to protect against the HCl-induced decline in resistance (R). Note: the one significant change with NaSCN shows that this monovalent anion was actually more harmful to the tissue than control.
Figure 2A:
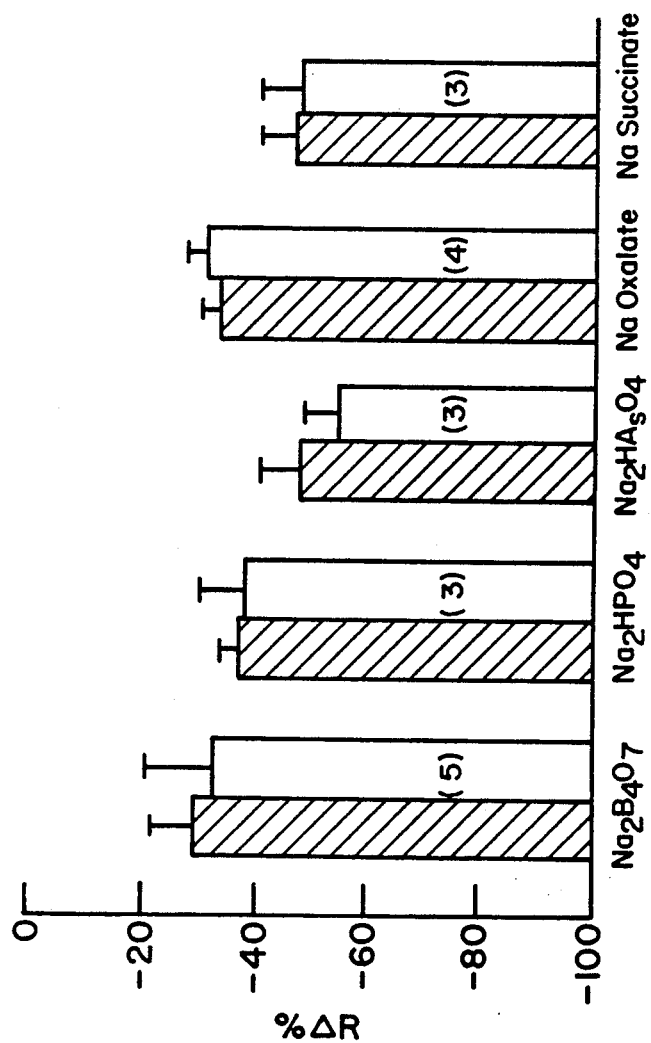
Figure 3:
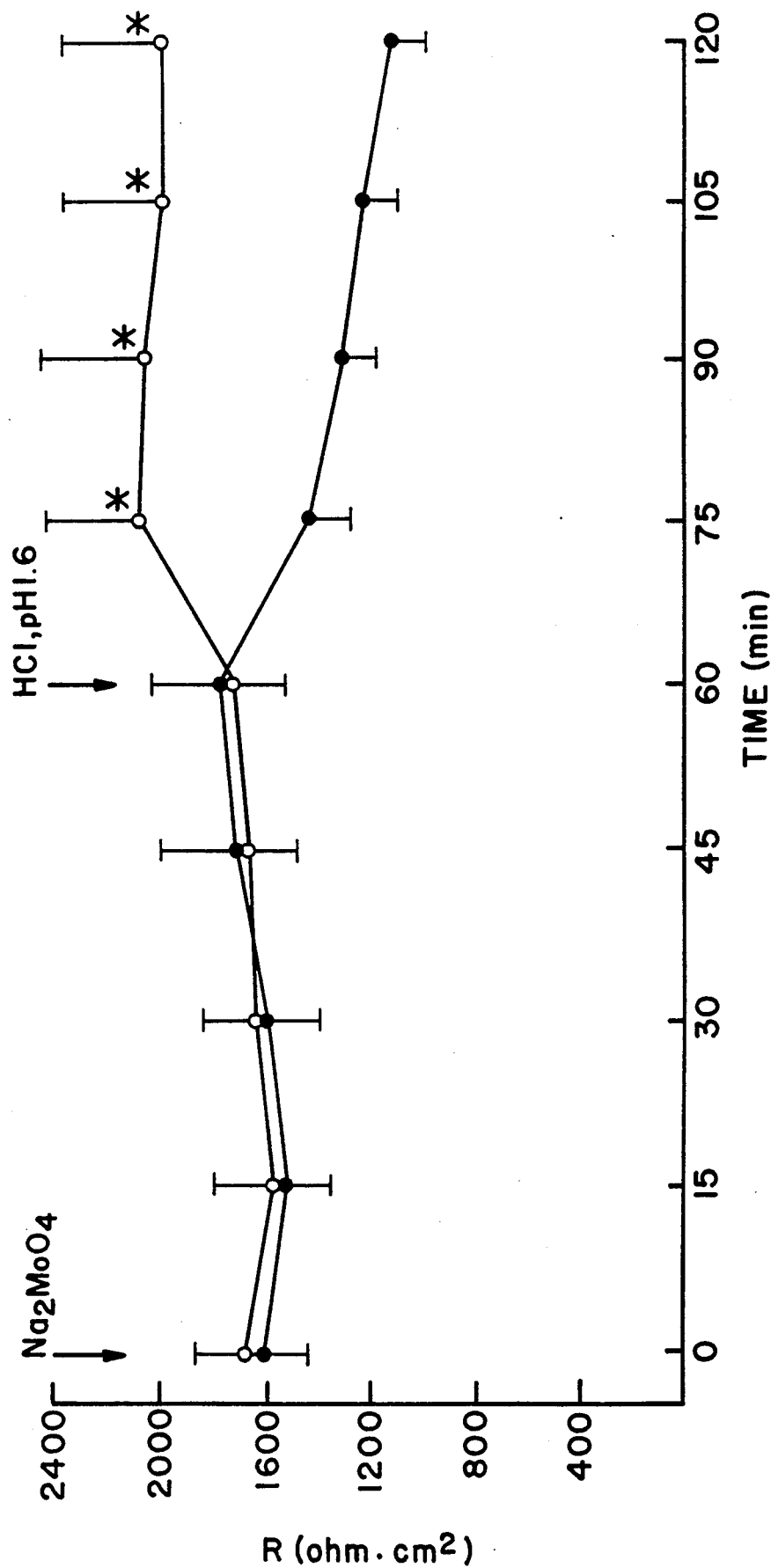
FIG. 3 shows that the addition of 38 mM sodium molybdate, a tetrahedral-shaped divalent oxy-anion, to the luminal bath has no significant effect on the baseline permeability of rabbit esophageal epithelia mounted in Ussing chambers as evident by the lack of change in baseline R. It is evident that tissues exposed to molybdate are protected against the decline in R upon luminal exposure to HCl (pH 1.6) for the duration of the exposure. Note: other electrical parameters measured but not shown (i.e. potential difference and short circuit current) were also not significantly changed by the addition of the test agents to the luminal bathing solution. n=5
Figure 4:
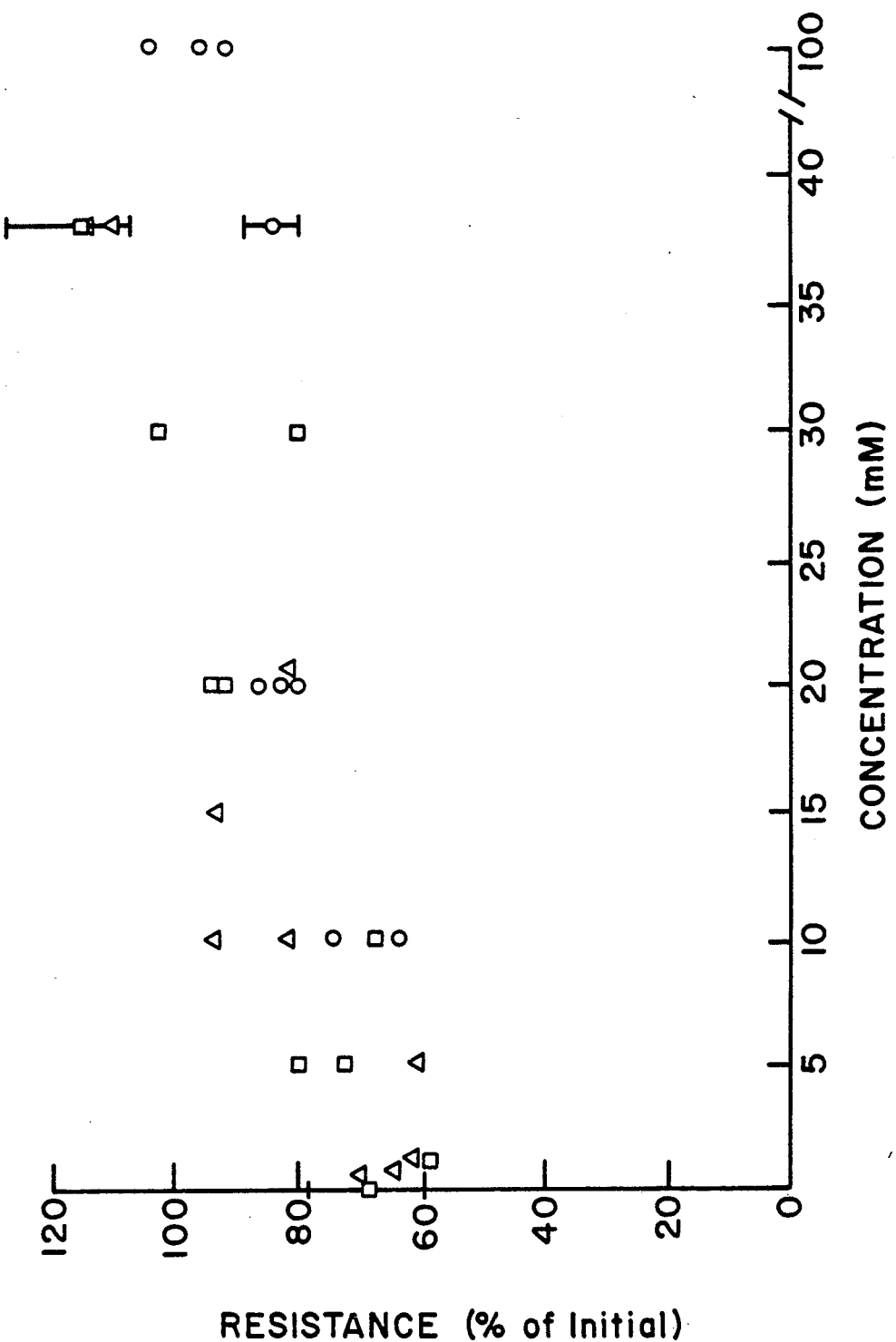
FIG. 4 shows that the lowest protective dose against acid damage to rabbit esophagus in vitro for three of the tetrahedral-shaped divalent oxy-anions, i.e. sulfate, chromate and molybdate, is approximately 10-20 mM. This experiment was performed similar to those of FIG. 1 in HCl-exposed rabbit esophageal epithelia mounted in Ussing chambers. R (% initial)=the percent change from preacidification values. Individual values are presented except for doses of 38 mM for which a mean of 5 experiments is shown and for values at zero mM which are the controls with no agent present.
Figure 5B:
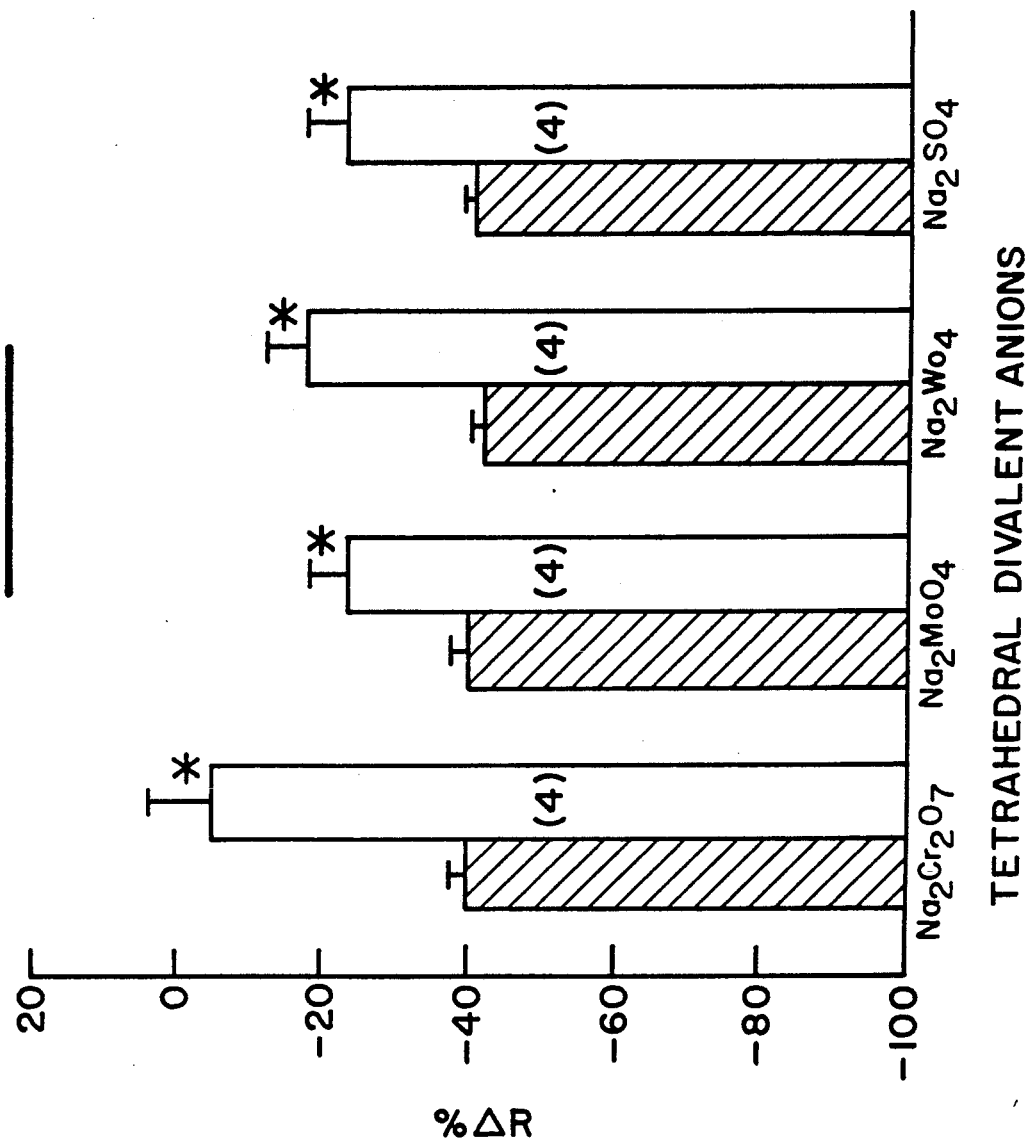
Figure 7:
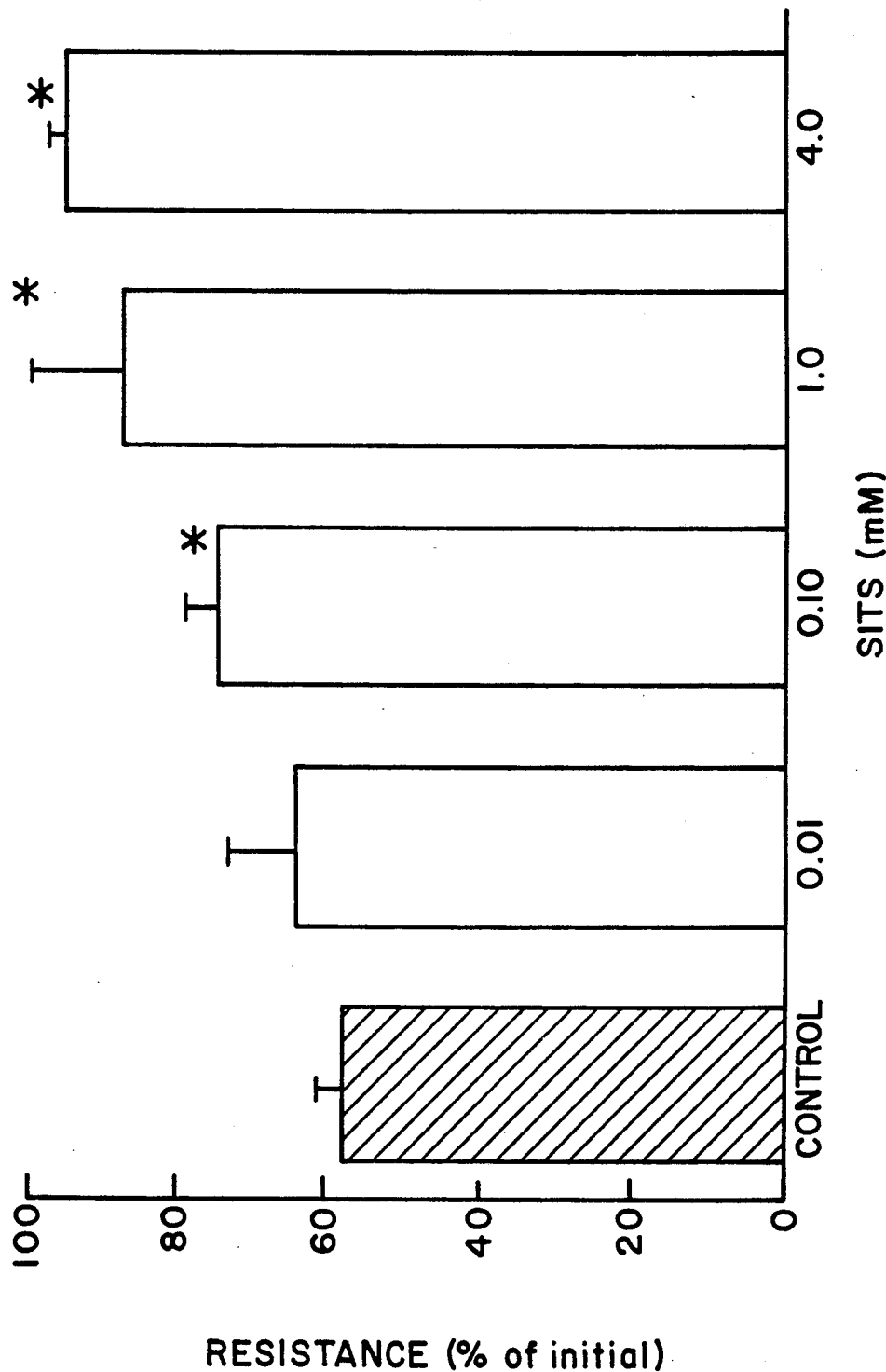
FIG. 7 shows that 4-acetamido-4'-isothiocyano-2,2'-stilbene disulfonate (SITS), a representative of the class of compounds known as sulfonates, when present in the luminal bath also protects against acid damage to rabbit esophageal epithelium mounted in the Ussing chamber, and further that this protection is afforded at doses that are 10-100 times lower than observed with compounds in the tetrahedral-shaped divalent oxy-anion group. Protection by luminal SITS is shown by its ability to block the HCl-induced decline in electrical resistance (R) upon exposure of tissue to luminal HCl (pH 1.6) for 1 h. Control tissues, are exposed to Ringer solution. R (% initial)=percent change from preacidification value. Values are mean ± SE, n=4-5.
Figure 8:
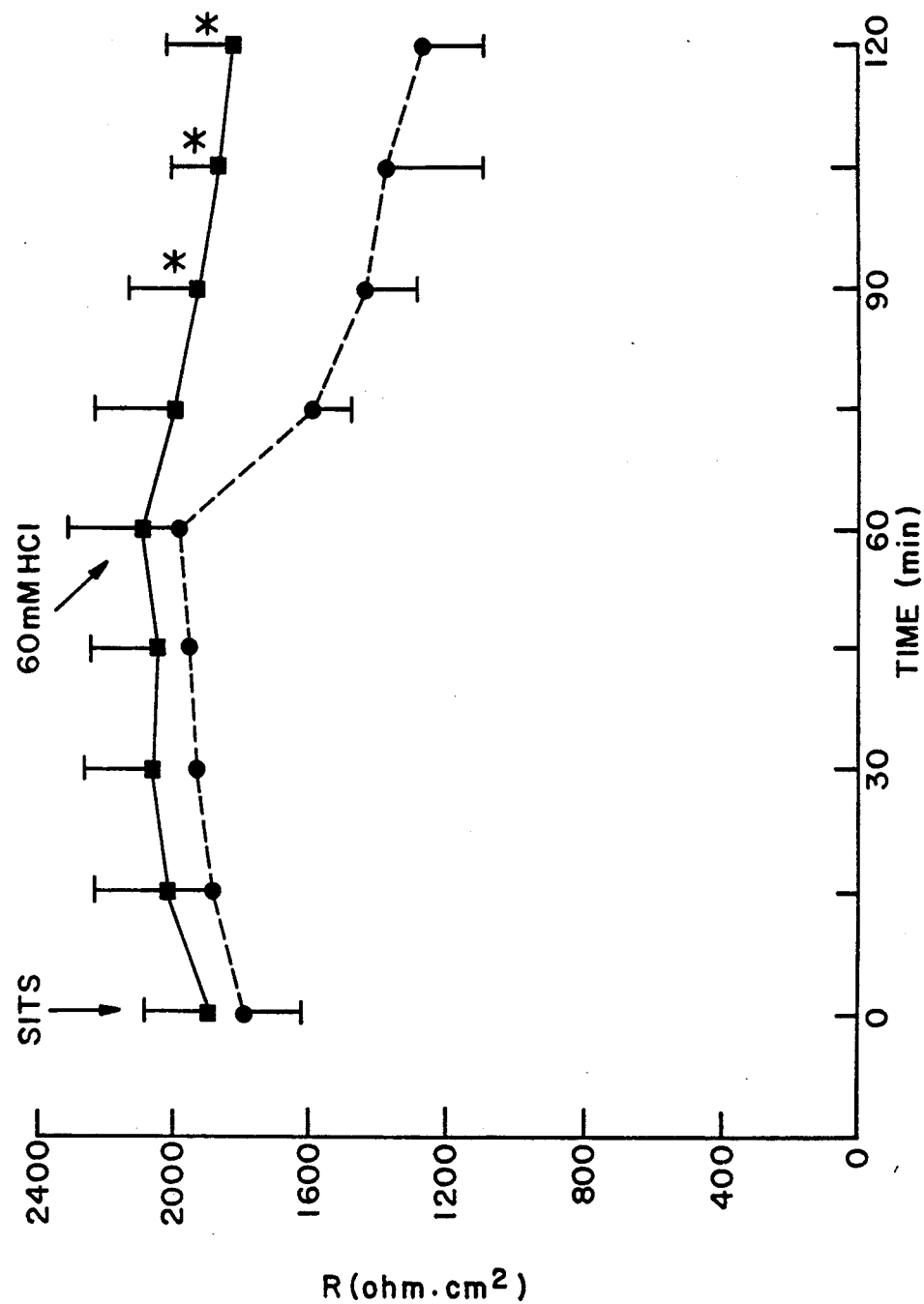
FIG. 8 shows that the addition of 4 mM 4-acetamido-4'-isothiocyano-2,2'-stilbene disulfonate (SITS), a sulfonate, to the luminal bath has no significant effect on the baseline permeability of rabbit esophageal epithelia mounted in Ussing chambers as evident by the lack of change in electrical resistance (R). Further despite the lack of change in baseline R, it is evident that tissues exposed to SITS are protected against the decline in R upon luminal exposure to HCl (pH 1.6) for the duration of the exposure. Note: other electrical parameters measured but not shown (i.e. potential difference and short circuit current) were also not significantly changed by the addition of the test agents to the luminal bathing solution. n=5
Figure 9:
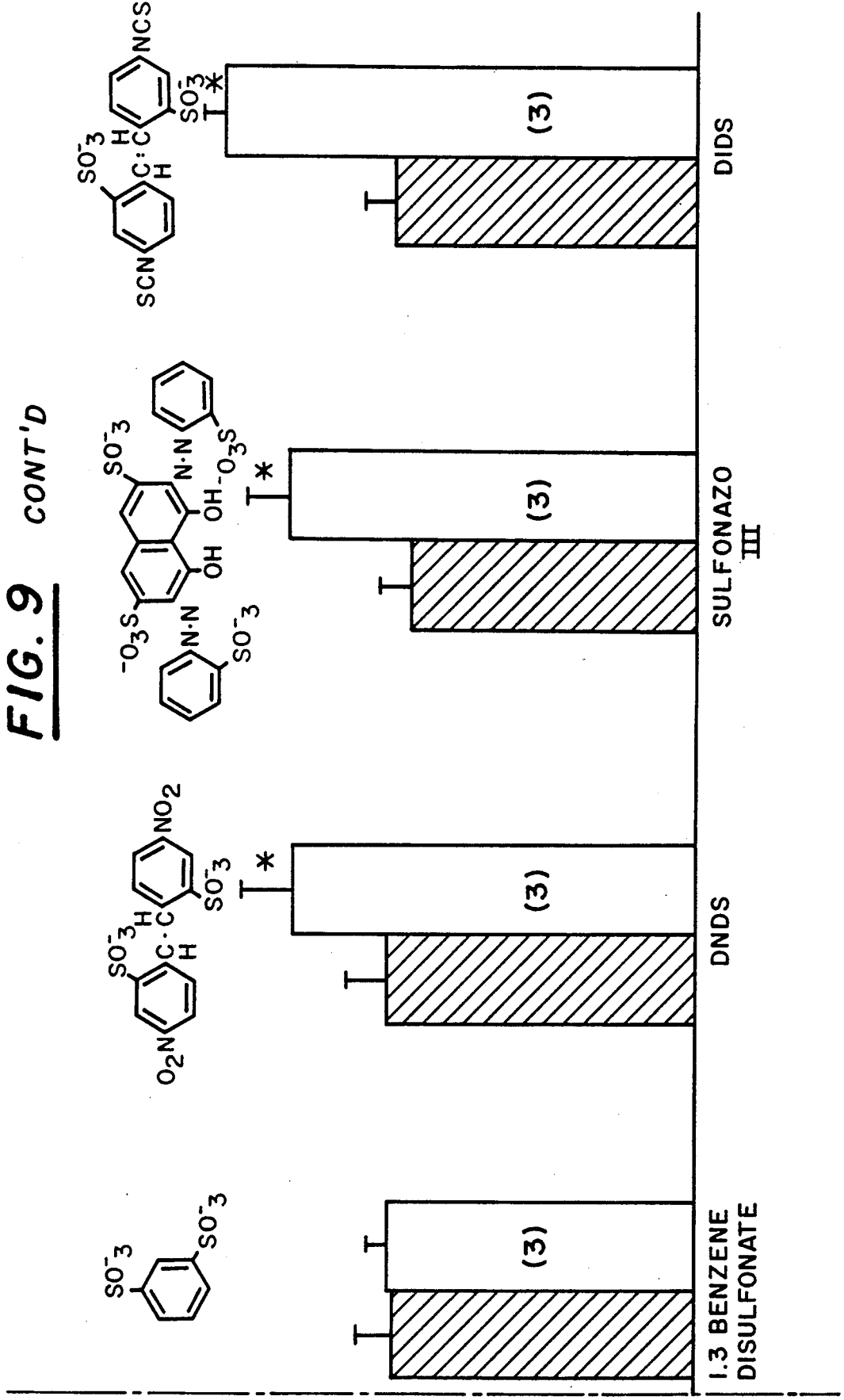
FIG. 9 shows that the protective effect of luminal 4-acetamido-4'-isothiocyano-2,2'-stilbene disulfonate (SITS) at 4 mM is also a property shared by a variety of sulfonated compounds with more than one aromatic ring in the molecule. This is shown by the ability of bromphenol blue, 8-anilino-naphthalene-1-sulfonate (ANS), dinitrodisulfonic acid stilbene (DNDS), sulfonazo III and 4,4'-diisothiocyano-2,2'-stilbene disulfonate (DIDS), when added to the luminal bath, to protect against the decline in resistance (R) of rabbit esophageal epithelia exposed to HCl (pH 1.6) while mounted in Ussing chambers. Control tissues were exposed to normal Ringer only. R (% initial)=percent change from preacidification value. Values are means ± SE, n=3-7.
Figure 10:
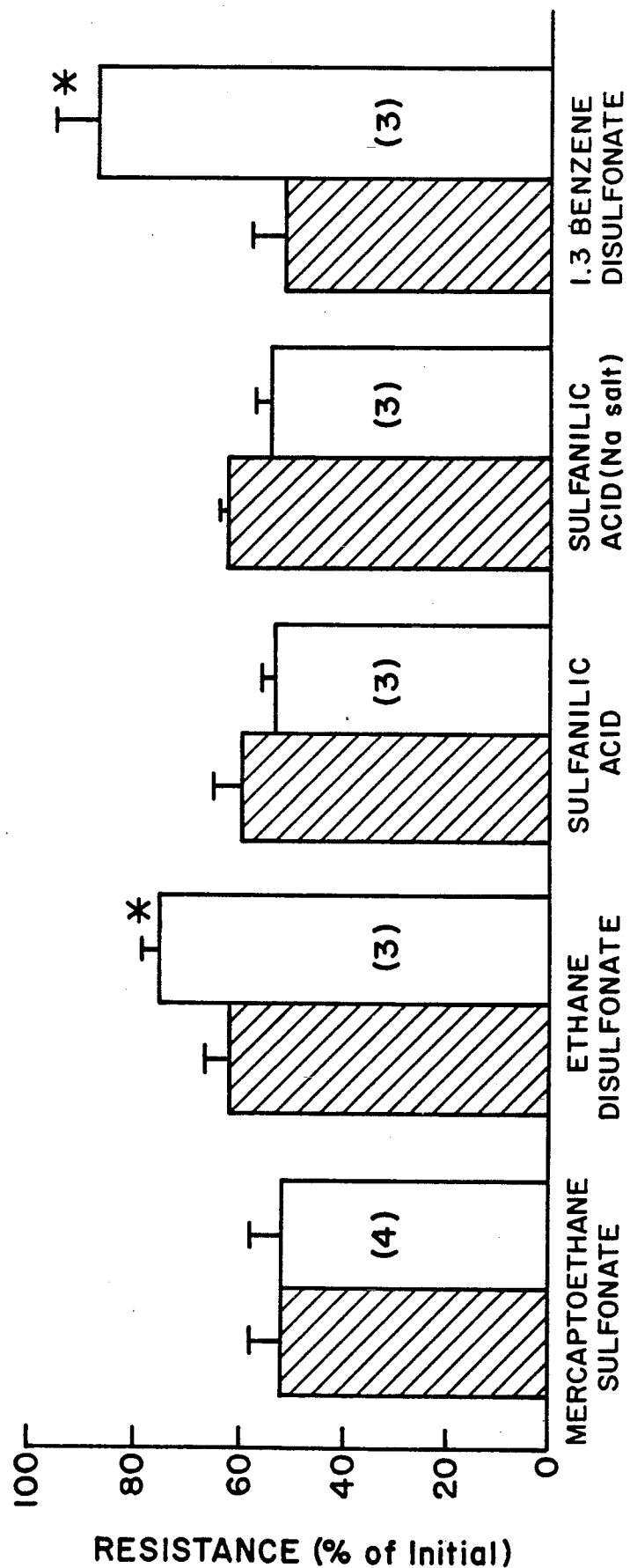
FIG. 10 shows that the disulfonates, ethane disulfonate and 1,3-benzene disulfonate, which were not protective at 4 mM, were protective against acid damage to rabbit esophageal epithelium at a higher dose of 40 mM. Note: even at this higher dose the aliphatic monosulfonate, mercaptoethane sulfonate, and the single ring aromatic monosulfonate, sulfanilic acid, were not protective. Protection is shown by the ability to prevent the decline in resistance (R) of rabbit esophageal epithelia mounted in Ussing chambers and exposed to luminal HCl, pH 1.6, for 1 h. Control tissues were exposed to normal Ringer only. R (% initial)=percent change from preacidification value. Values are means ±SE, n=3-4.
Figure 12C:
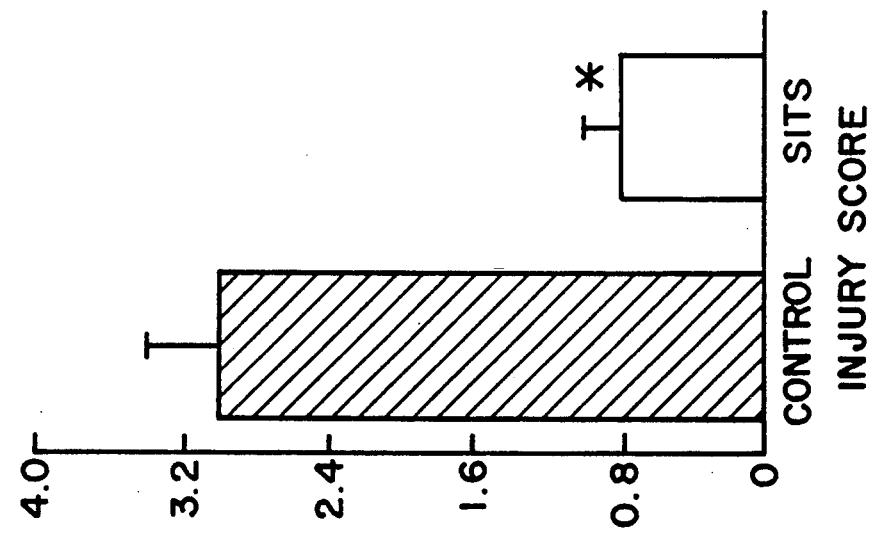
FIG. 12 shows that 4-acetamido-4'-isothiocyano-2,2'-stilbene disulfonate (SITS), a sulfonate, not only protects against acid damage to rabbit esophageal epithelium in vitro but also protects in vivo. In these in vivo experiments rabbit esophagi were cannulated and perfused with 120 mM HCl-20 mM NaCl in the presence or absence of SITS, 8 mM, for 1 h. Resistance and mucosal-to-serosal mannitol flux ($J^{man}$ms) were performed on tissues mounted in Ussing chambers after exposure to HCl in vivo. Injury was scored as follows: 0=normal epithelium, 1=intracellular/extracellular edema, 2=patchy intraepithelial cell necrosis, 3=diffuse necrosis, and 4=ulceration (transmucosal necrosis). SITS is shown to protect the esophagus against acid damage in vivo both morphologically by a lower injury score on light microscopy and functionally by a lower permeability to mannitol and higher electrical resistance (R). Values are reported as mean ± SE, n=7.
Figure 12B:
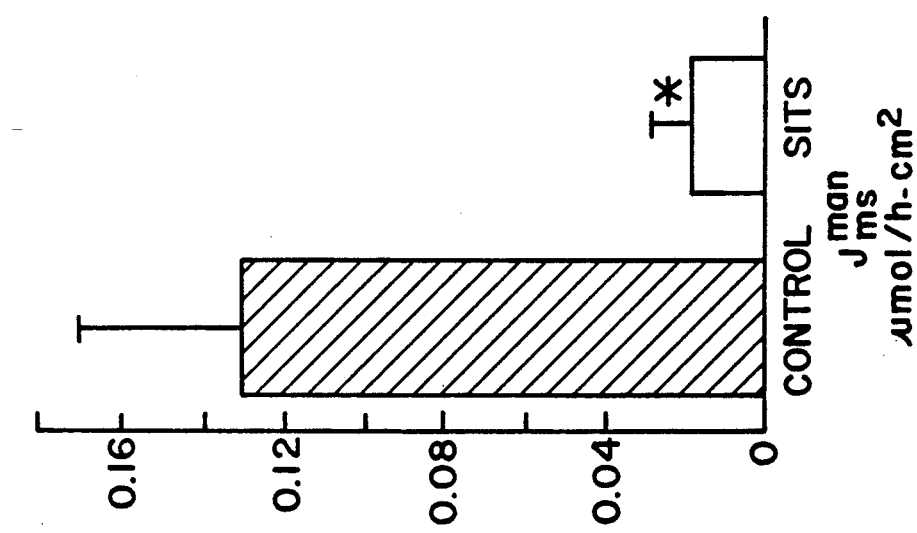
Figure 12A:
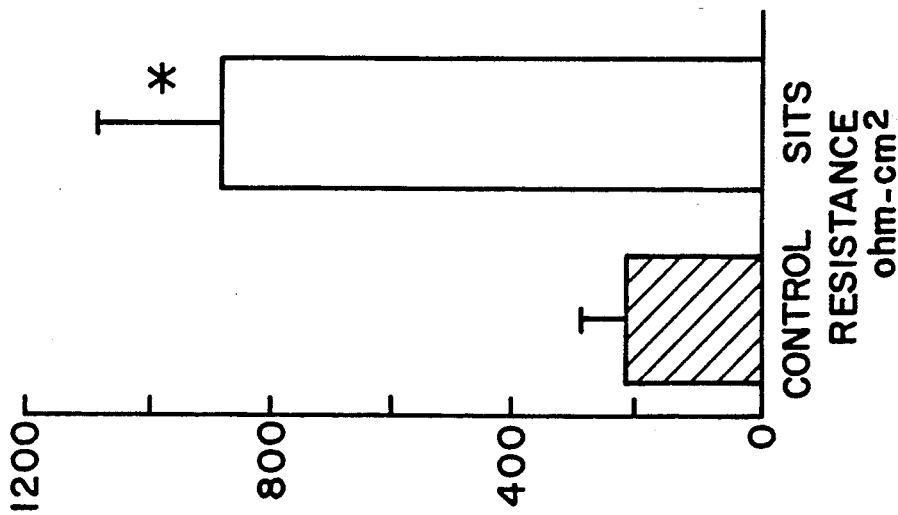
Figure 13:
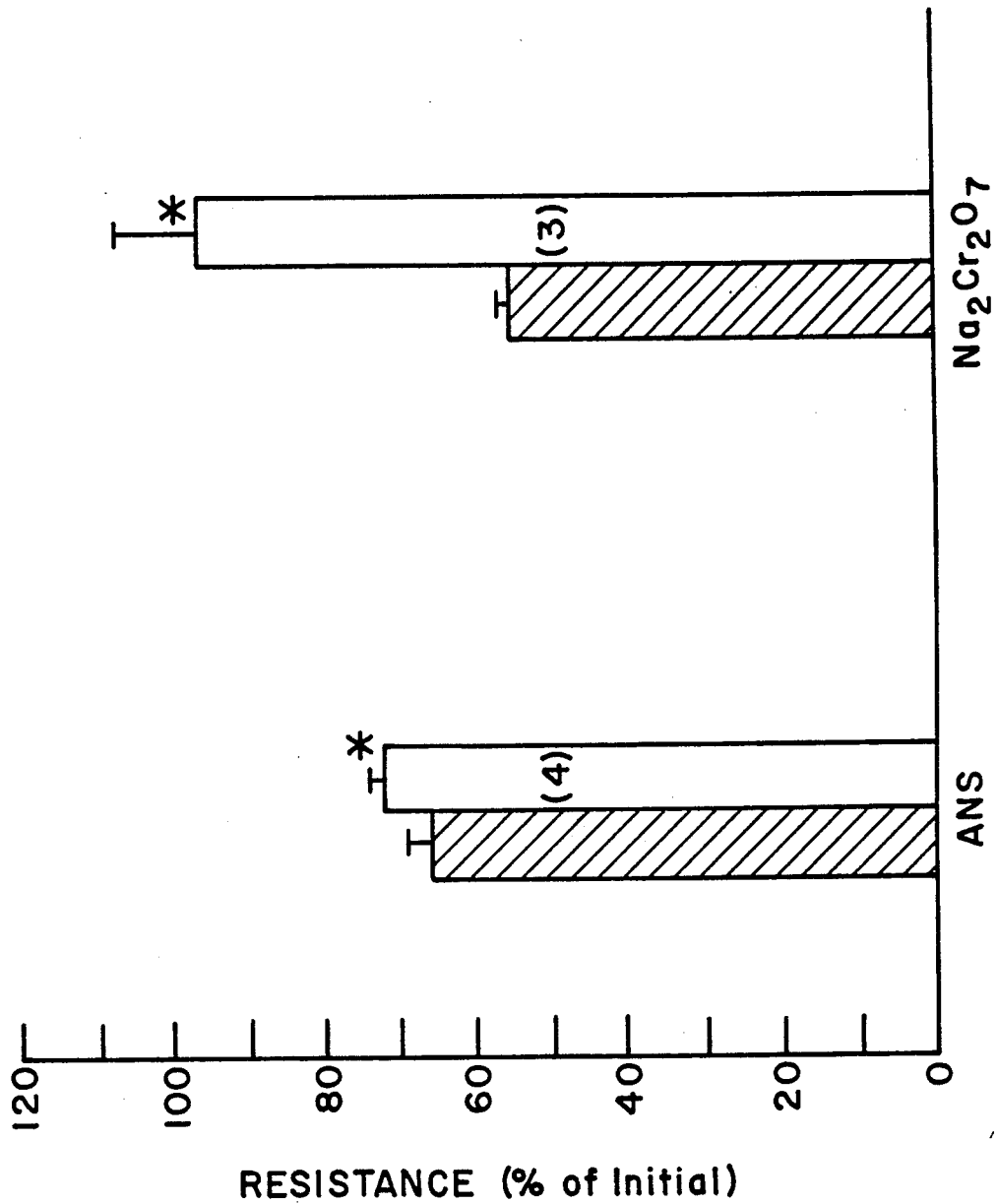
FIG. 13 illustrates that transient (1 min) exposure of tissues to a protective agent from either the sulfonate class, 8-anilino-naphthalene-1-sulfonate (ANS), 4 mM, or the tetrahedral-shaped divalent anion class, sodium dichromate, 38 mM, can protect even when the exposure to acid (HCl, pH 1.6 1 h) is delayed for up to 5 hours. Note: 1 min is used as the time for transient contact because it is as fast as the experiment can technically be carried out. Protection by these compounds is likely to occur with much less time of contact.
Figure 14:
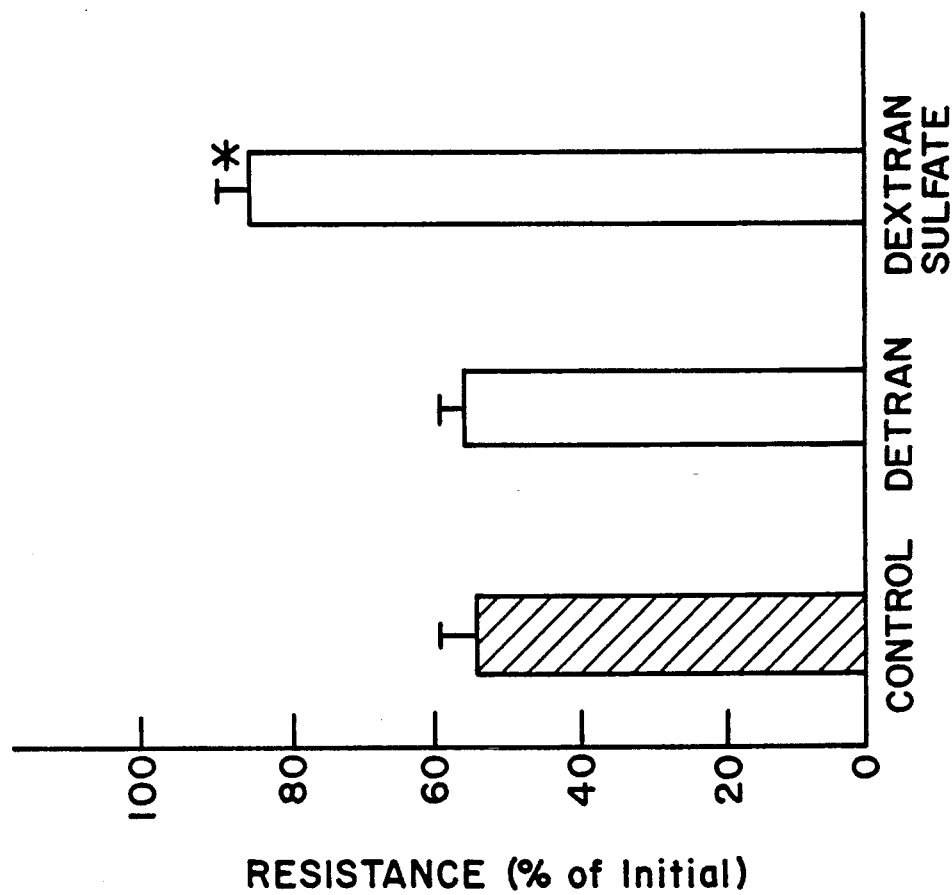
FIG. 14 shows that 1 h luminal pretreatment with dextran sulfate (4 mM) but not an equimolar amount of dextran is protective against the HCl-induced decline in electrical resistance (R) of rabbit esophageal epithelia mounted in Ussing chambers. Note: this is another example of protection by compounds containing a sulfate ester linkage (O—SO$_3^-$). Control tissues were exposed to normal Ringer solution before luminal acidification with HCl (pH 1.6) for 1 h. R (% initial)=percent change from preacidification value. Values are means ± SE.

Table 1. Protection of dog buccal epithelium against luminal acid injury by molybdate and SITS. The table shows that luminal 38 mM sodium molybdate, a tetrahedral-shaped divalent oxy-anion, or luminal 4 mM 4-acetamido-4'-isothiocyano-2,2'-stilbene disulfonate (SITS), a sulfonate, can protect the moist stratified squamous epithelium of dog buccal mucosa against acid damage. Protection is shown by the ability to prevent the decline in resistance (R) of dog buccal epithelium exposed to luminal HCl for 1 h in the Ussing chamber. Note: this low luminal pH is less well tolerated by buccal than by esophageal epithelium and consequently protection while exhibited in buccal epithelium by the agents is much less dramatic.

TABLE 1

Effect of 15 min. pretreatment with protective agents on the electrical resistance of dog buccal mucosa mounted in the Ussing chamber and luminally acidified (pH 1.5) with HCl for 1 h.

| PRETREATMENT AGENT | RESISTANCE (ohm · cm$^2$) | |
| --- | --- | --- |
| | PRE ACID | POST ACID |
| SITS (4 mM) | 747 ± 118 | 224 ± 25* (32 ± 6%)* |
| Na$_2$—MoO$_4$ (38 mM) | 505 ± 65 | 239 ± 44* (47 ± 7%)* |
| Ringer Control | 647 ± 101 | 90 ± 13 (15 +3%) |

*p < 0.05 compared to paired control
Values reported as mean + SE
n = 4
Numbers in parentheses express the post acid value as a percent of the pre acid agent value.

DETAILED DESCRIPTION OF THE INVENTION

The present invention describes:

1) a mechanism for protection of moist stratified squamous epithelia against injury from exposure to luminal HCl and other noxious luminal substances such as N-acetylcysteine. The mechanism is by stabilization of the intercellular junctions so as to block the increase in paracellular permeability that accompanies exposure to these noxious luminal substances, 2) the identification of three chemical reactive groups and three classes of compounds derived from them that when topically applied protect moist stratified squamous epithelia against damage from luminal HCl and N-acetylcysteine by stabilizing their intercellular junctions so as to block the increase in paracellular permeability that normally accompanies such exposure.

The three reactive groups are:
a) X-SO$_3^-$, where X represents an oxygen or carbon linkage covalently or ionically bound to an organic or inorganic molecule, and the tetrahedral-shaped divalent oxy-anionic groups:
b) XO$_4^=$ and
c) X$_2$O$_7^=$, where X represents an element from group VIb of the periodic table or sulfur from group VIa covalently or ionically bound to an organic or inorganic molecule.

The three classes of chemical compounds derived from them are:
a) the sulfonates, e.g. 4-acetamido-4'-isothiocyano-2,2'-stilbene disulfonate (SITS), 8-anilino-naphthalene-1-sulfonate (ANS), dinitro-disulfonic acid stilbene (DNDS), sulfonazo III, 4,4'-diisothiocyano-2,2'-stilbene disulfonate (DIDS), bromphenol blue,
b) the sulfate esters, e.g. sucrose octasulfate, dextran sulfate, and
c) the tetrahedral-shaped divalent oxy-anions, e.g. sodium chromate, sodium dichromate, sodium molybdate, sodium tungstate, sodium sulfate, and 3) the likelihood that the protection afforded by the classes of compounds illustrated in (2), other existing or newly synthesized compounds in these classes or with the designated reactive groups are likely to have clinical applicability for the prevention of reflux symptoms and esophagitis in humans because they:
a) act topically and so can be administered orally,
b) have a rapid onset of action (≦1 min),
c) have a long duration of action (≧5 h),
d) can be administered in low dose (0.1–4 mM for sulfonates/sulfate ester and 20–40 mM for tetrahedral-shaped divalent oxy-anions, and
e) have the potential for low toxicity because of poor absorption and, despite avid tissue binding, lack of effect on baseline permeability or transport of the tissue. Note: poor absorption was shown by fluxes of radiolabelled $^{35}SO_4^=$ and $^3H$-DIDS; for sulfate, $n=4$, the values were $0.0036\pm0.002$ $\mu mol/h\cdot cm^2$ and in two experiments with DIDS the values were 0.0003 and 0.0005 $\mu mol/h\cdot cm^2$.

The new discoveries found during the current investigations that form the basis of the present invention are those described in (1), (2), and (3) above.

Furthermore the classes and the agents described above are more potent protectors against acid injury to esophageal epithelia than the previously reported sulfate ions. This may be a result of more avid binding to the same receptor in esophageal epithelium as sulfate since it is evident that many of these same compounds bind to sulfate receptors inhibiting sulfate transport in other tissues, e.g. kidney and placenta. Some additional experimental data in support of the protective agents being bound to protein within esophageal epithelium was shown by exposing the tissue briefly to luminal radiolabelled-sulfate ($^{35}SO_4=$) or radiolabelled-sulfonate ($^3H$-DIDS) and by the inventors being unable to subsequently extract any of the radiolabelled-agent from the tissue after homogenization and extraction with methanolchloroform, a lipid solubilizing procedure (Folch J., Lees M., Stanley G. H. A simple method for the isolation and purification of total lipids from animal tissue. J Biol Chem 1957; 226: 497–509).

Proof that the above agents protect against acid injury to esophageal epithelium was carried out in rabbit esophagus both in vitro and in vivo. In vitro studies consisted of mounting healthy rabbit esophageal epithelia in Ussing chambers, exposing them on the luminal surface continuously or transiently to a test agent and monitoring the change in electrical resistance, a marker of tissue permeability, upon luminal acidification with HCl (see methods for details). In healthy control tissues HCl exposure reduced resistance with time while protection by an agent is shown by its ability to prevent the decline in resistance. The fact that the decline in resistance indicates increasing permeability of the tissue and the reasons for it being a forerunner to the development of tissue necrosis has been discussed above.

Compounds of the sulfonate, sulfate ester and tetrahedral-shaped divalent oxy-anion class were shown to be protective either when present in the luminal bath at the time of acidification or when tissues were only briefly (1 min) exposed to the compounds before acidification of the luminal bath. This was evident in their ability to prevent the HCl-induced decline in resistance shown to occur in the simultaneously studied and electrically (by resistance) paired control tissues. In addition with some compounds even with brief tissue exposure (1 min) protection against acid injury could be shown and protection with brief exposure shown even when luminal acidification was delayed for 5 hours. This establishes that protective compounds in these two classes can have a long duration of action even with minimal tissue contact time.

Protection by these compounds was not only shown in vitro by the ability to prevent the decline in resistance of HCl-exposed rabbit esophageal epithelia in the Ussing chamber but was confirmed in vivo using the HCl-perfused rabbit esophagus model (see methods for details). In these experiments tissues were exposed in vivo to an isosmotic solution containing a protective agent or to an isosmotic control solution prior to being perfused with HCl for 1 h in vivo. After exposure a number of parameters were used to define if tissues were damaged or protected including: gross inspection, light microscopy, electrical resistance and permeability to mannitol (mannitol flux), the latter two parameters obtained by mounting a section of HCl-perfused epithelium in the Ussing chamber. For two classes of compounds, the sulfonates (SITS the test agent) and tetrahedral-shaped divalent oxy-anions (sodium molybdate the test agent) protection was documented by all criteria when compared to control animals. This confirmed that protection in vitro, that is by blocking the HCl-induced decline in resistance, was indeed predictive of a compounds ability to protect in vivo. Further and supporting protection as a general characteristic of both tetrahedral-shaped divalent oxy-anions and compounds like the sulfonates bearing the $X$—$SO_3^-$, reactive group, this same sequence has been previously reported (see prior references) for sodium sulfate, sulfate ions being a tetrahedral-shaped divalent oxy-anion ($XO_4^=$ group), and for sucrose octasulfate which contains the sulfate ester $O$—$SO_3^-$ group.

These classes of protective agents were also shown to protect against acid injury to another type of moist stratified squamous epithelia from another species, that is the dog buccal epithelium. This indicates that protection against acid injury by tetrahedral-shaped divalent oxy-anions and $X$—$SO_3^-$ containing compounds of which sulfonates represent one important group are a general phenomena extending to other moist stratified squamous epithelia (e.g cornea, cervix, vagina, tongue, gingiva, palate, pharynx, rumen of animals). A recent example to further support this comes from a report by Yanagisawa and colleagues (Yanagisawa T., Wakabayashi S., Tomiyama T., Yasunami M., Takase K. Synthesis and anti-ulcer activities of sodium alkylazulene sulfonates. Chem Pharm Bull 1988; 36:641–647). These investigators were developing compounds for use in the treatment of peptic ulcer, basing their research on the known protective agents "guaiazulene" and its hydrophilic derivative, guaiazulene sodium sulfonate (Okabe S., Takeuci K., H. and K. Takagi. Pharmacometrics 1975; 9:31). Interestingly, and supporting the present inventors' concepts, they found that the sulfonate derivates were the most potent for protection against ulceration of the rat forestomach (Shay model)—the forestomach being an area lined by stratified squamous epithelia. Further and in contrast to the present inventors' work they attributed the mechanism of action of these compounds to the ability of guaiazulene and its derivates to inhibit the activity of the enzyme pepsin rather than, as suggested herein, by the ability of the sulfonate groups to stabilize the intercellular junctions of moist stratified squamous epithelium so as to protect them against injury by luminal HCl.

The present invention relates to the protection of the above moist stratified squamous epithelia against acid injury by administering the protective compound in such a way as to make contact with the luminal surface of the tissue. This includes such general methods of administration as topical application and perfusion via a tube for all moist stratified squamous epithelia, oral ingestion for oropharyngeal, rumen and esophageal epithelium, mouth rinse (for oral epithelium), eye rinse (for cornea) and douche (for cervix or vagina).

While the present invention is directed specifically towards protection of moist stratified squamous epithelia against acid injury by topically administering a compound containing one of the reactive groups or belonging to one of the classes of agents based on them, the present invention is equally applicable to protection of moist stratified squamous epithelia against injury from other noxious luminal agents that damage the tissue similar to that of acid—that is by increasing junctional (paracellular) permeability. This concept is demonstrated by the ability of the defined cytoprotective compounds to protect rabbit esophageal epithelia against the decline in resistance upon exposure to luminal N-acetylcysteine. N-acetylcysteine is known to break disulfide bonds and presumably increases permeability through the paracellular pathway because the initial reductions in electrical resistance are not associated with cell edema or necrosis (cell edema or necrosis would likely occur if such large increases in permeability occurred across the cell membrane rather than the junction). The observation that the decline in resistance is blocked by a cytoprotective compound that also protects against the HCl-induced decline in resistance also supports that damage by acid and N-acetylcysteine occur at the same site, that is at the intercellular junctions. If injury to moist stratified squamous epithelia from infectious agents (e.g., bacteria, viruses, yeast or fungi), chemicals (e.g., lye, bleach, tobacco products) and/or other luminal environmental conditions (e.g., heat, hypertonicity) occurs by increasing the permeability through the intercellular junctions, then the presently described cytoprotective agents by virtue of their stabilizing effect on the intercellular junctions would exert a protective action.

Treatment by these compounds would consist of topical application to a moist stratified squamous epithelia of either an existing or newly synthesized compound containing at least one of the defined reactive groups defined in (2) above, but usually as shown for the most effective sulfonates has more than one reactive group, that is $R(XSO_3-)_n Y_n^+$ (where n is a positive integer, Y represents an element in group IA of the periodic table, and X is an oxygen or carbon linkage between the $-SO_3-$ group and R, R representing an organic or inorganic group covalently or ionically bonded to X. The cytoprotective compounds would also include any precursor compounds that when subjected to an acidic or other chemical environment are reduced to yield one of the defined reactive groups in (2).

Examples of cytoprotective compounds containing an $-X-SO_3-$, reactive group, where X is a carbon as in the sulfonates or oxygen as in the sulfate esters include but are not limited to: 4-acetamido-4'-isothiocyano-2,2'-stilbene disulfonate (SITS), 8-anilino-naphthalene-1-sulfonate (ANS), dinitro-disulfonic acid stilbene (DNDS), sulfonazo III, 4,4'-disothiocyano-2'2-stilbene disulfonate (DIDS), bromphenol blue, sucrose octasulfate and dextran sulfate.

Examples of cytoprotective compounds containing a tetrahedral-shaped divalent oxy-anion of the transition metals in group VIb of the periodic table or sulfur in group VIa include but are not limited to: sodium dichromate, sodium molybdate, sodium tungstate, sodium sulfate.

Moreover agents that can be used for prevention of acid injury to the esophageal epithelia in humans whether existing or newly synthesized using the configurations outlined above may be effective for prevention of reflux disease in humans.

In a preferred embodiment, a cytoprotective compound having one of the defined configurations described above and shown to be safe for use in humans would be administered orally to a subject with reflux esophagitis. An adult of average size would be expected to ingest in liquid or powder form the equivalent of 0.1–4 mM of the sulfonate or sulfate-ester type agents or 10–20 mM of the tetrahedral-shaped agent from two-to-four times per day (total does in milligrams/grams would depend upon the molecular weight of the compound). Contact of the esophageal epithelium even briefly with the ingested agent would then be expected to prevent further acid damage to the tissue for many hours.

Methods

I. For tetrahedral-shaped divalent oxy-anions.

In vitro. White New Zealand rabbits weighing 8–9 lbs. were killed with an overdoses of pentobarbital sodium (60 mg/ml), and the esophagus was removed. The esophageal epithelium was stripped of its muscle layers and mounted in Ussing chambers. The luminal and serosal sides were bathed with Ringer solution (in mM) 140 $Na^+$, 119.8$Cl^-$, 5$K^+$, 25 $HCO_3^-$, 1.2 $Mg^{2+}$, 1.2 $ca^{++}$, 2.4 $HPO_4^=$, 0.4 $H_2PO_4^-$ (280 mosmoml/kg $H_2O$, pH 7.4 when gassed with 95% $O_2$/5%, CO, maintained at 37° C.). Luminal and serosal solutions of similar volume and composition were in contact with calomel and Ag-AgCl electrodes via agar bridges. The electrodes were connected to an automatic voltage clamp for measurements of potential differences (PD) and short-circuit current (Isc). Tissues were continuously short-circuited except for brief intervals (2–3 sec) when the open circuit PD was read. Resistance (R) was calculated using Ohm's law from the open circuit PD and the Isc. After 45 min for equilibration, epithelia were paired by R (R within 25%). One of the pair was then exposed luminally to a sodium salt (38 mM) of a tetrahedral-shaped divalent oxy-anion, a non-tetrahedral shaped divalent anion, or a monovalent anion. The other tissue was exposed to iso-osmotic sodium chloride (NaCl) as control. After 1 h of treatment, luminal solutions were titrated to pH 1.6 and an equimolar amount of choline chloride added to the serosal bath to balance osmolality and to limit ionic diffusion to $H^+$ alone. Controls required 60 mM HCl to titrate pH to 1.6. All other agents except the following required similar amounts of HCl to titrate the bath to pH 1.6: chromate 108 mM, tungstate 119 mM, molybdate 122 mM, sulfate 72 mM, and monohydrogen phosphate 118 mM. After initial titration, luminal pH for all agents remained constant throughout the experiment. After luminal acidification, R was monitored for 1 h.

In vivo. White New Zealand rabbits weighing between 8–9 lbs. were anesthetized with a 1:1 mixture of diazepam (5 mg/ml) and pentobarbital sodium (60 mg/ml). The esophagus was cannulated in the neck and in the abdomen just above the esophagogastric junction. The two cannulas were connected via a Buchler polystaltic pump so that 50 ml of an HCl solution could be perfused and recirculated through the esophagus (37° C., 10 ml/min). Esophagi were initially perfused for 30 min with 38 mM $Na_2MoO_4$-90 mM NaCl (242 mosm/kg $H_2O$) or an iso-osmotic solution of saline (150 mM NaCl) (284 mosm/kg $H_2O$) as control. After these perfusions, esophagi of all animals were flushed with 50 cc normal saline. Esophagi were then perfused, using a recirculating system, for 1 h with 120 mM HCl-20 mM NaCl, pH 1.0. After acid exposure, the perfusate was collected for determination of volume and calculation of $H^+$ content. $H^+$ content was determined by titration of duplicate 10 ml aliquots to pH 7 with 1 N NaOH using a Radiometer PHM82 pH meter (Radiometer, Copenhagen, Denmark). H+ efflux ($J^H$+m-s) (loss from the lumen) was determined by measuring the difference between the amount of H+ in solution before and after the 1 h esophageal perfusion. H+ efflux was reported in ueq h$^{-1}$ cm$^{-2}$ by dividing the total H+ lost from the perfusate by the area of esophagus exposed to solution. The area of exposure was determined, after killing the animal with an overdose of pentobarbital and excising the esophagus, by measuring the length and width of esophagus between the two cannulas.

After removal, the esophagus was inspected for gross lesions and a section from the distal third obtained for mounting in the Ussing chamber. This section was stripped of its muscle layers and mounted in 10 mM mannitol-Ringer solution in the Ussing chamber for assessment of permeability by measurements of R and mucosal-to-serosal [$^{14}$C]mannitol flux ($J^{man}$m-s). [$^{14}$C]mannitol fluxes were performed by adding 10 μCi of [$^{14}$C]mannitol to the luminal bath. After a 15 min equilibration period, R was recorded, and five 15 min fluxes of [$^{14}$C]mannitol were determined. Flux data reported represent the mean for the five flux periods. The remainder of the HCl-exposed esophagus was fixed in 2% paraformaldehyde, 4% glutaraldehyde in 0.1N phosphate buffer, pH 7.4, cut into equal-sized sections and stained with hematoxylin and eosin for evaluation by light microscopy. Histology slides were coded and read by the examiner with no knowledge of the treatment group. For each section the presence or absence of necrosis was noted and when present, a percentage appended to reflect the linear extent of the epithelium having necrosis.

Statistical significance was determined using Students's t-test and all data were reported as the mean ± standard error (SE).

II. For the sulfonates and sulfate esters.

In vitro. White New Zealand rabbits weighing 8-9 lbs were killed with an overdose of pentobarbital sodium (60 mg/ml), and the esophagus was removed. The esophageal epithelium was stripped of its muscle layers and mounted in Ussing chambers. The luminal and serosal sides were bathed with Ringer solution (in mM) 140 Na+, 119.8 Cl−, 5.2 K+, 25 HCO$_3$—, 1.2 Mg$^{2+}$, 1.2 Ca$^{2+}$, 2.4 HPO$_4^{2-}$, 0.4 H$_2$PO$_4$— (280 mosm/kg H$_2$O), pH 7.4 when gassed with 95% O$_2$— 5% CO$_2$ maintained at 37° C. Luminal and serosal solutions of similar volume and composition were in contact with calomel and Ag-AgCl electrodes via agar bridges. The electrodes were connected to an automatic voltage clamp for measurements of potential difference (PD) and short-circuit current (Isc). Tissues were continuously short-circuited except for brief intervals (2-3 s) when the open circuit PD was read. Resistance (R) was calculated using Ohm's law from the open circuit PD and the Isc.

To assess a compounds ability to protect rabbit esophageal epithelia against acid injury, after equilibration (approximately 45 min after mounting), tissues paired by R (R within 25%) were exposed luminally to a test agent (e.g. SITS) while the other served as untreated control. After 1 h, the luminal solutions were acidified with HCl to pH 1.6 (note: some agents acted as weak buffers requiring from 0-40 mM more HCl to reach pH 1.6 than others) and equimolar amounts of choline chloride added serosally to balance osmolality and limit ionic diffusion to H+ alone. PD, Isc and R were monitored every 15 min through the experiment.

In some experiments, tissues were pretreated luminally with SITS for 1 h and the SITS-containing luminal solution replaced with normal Ringer prior to luminal acidification with HCl. Electrical parameters were monitored every 15 minutes as described above.

Junction potentials were determined for all solutions used in these experiments. Solutions reflecting those present under experimental conditions were placed in separate beakers and the beakers used in pairs to reflect luminal or serosal bathing solutions for tissues mounted in the Ussing chamber. The results, however, showed that all junction potentials were insignificant being <1 mV and so were not corrected for in the presentation of results.

In vivo. Protection against acid injury was assessed using a perfusion technique. White New Zealand rabbits weighing 8-9 lb were anesthetized with a 1:1 mixture of diazepam (95 mg/ml) and pentobarbital sodium (60 mg/ml) and strapped to an animal board covered with a heating pad to maintain body temperature at 37° C. The esophagus was cannulated in the neck and in the abdomen just above the esophagogastric junction. The two cannulas were connected via a Buchler polystaltic pump so that 50 ml of an HCl solution could be perfused and recirculated through the esophagus (37° C., 10 ml/min). Esophagi were perfused with saline for 30 min followed by 120 mM HCl-20 mM NaCl for 1 h (control) or saline+8 mM SITS followed by 120 mM HCl-20 mM NaCl+8 mM SITS. SITS - containing perfusates had approximately the same osmolality (276 vs 263 mosmol/kg H$_2$O for controls) and Na content (36 mM vs 20 mM Na for controls) as that of the saline-controls. After perfusion of the esophagus, the rabbits were killed with an overdose of pentobarbital sodium. The esophagus was removed and inspected for gross lesions. One section of esophagus was stripped of its muscle layers and mounted in 10 mM mannitol-Ringer solution in the Ussing chamber for measurements of R and for assessment of permeability by measuring the mucosal-to-serosal [$^{14}$C]mannitol flux ($J^{man}$ms). [$^{14}$C]mannitol was added to the luminal bath and after a 15-min equilibration period, R was recorded, and five 15-min fluxes of [$^{14}$C]mannitol were determined. Mean data for the five flux periods is reported. A second section of esophagus was fixed (2% paraformaldehyde, 4% glutaraldehyde, 0.1N phosphate buffer, pH 7.0) and stained with hematoxylin and eosin for evaluation by light microscopy. Lesions were recorded and scored by an examiner without knowledge of treatment groups using the following system: 0=normal epithelium, 1=intracellular/extracellular edema, 2=patchy intraepithelial cell necrosis, 3=diffuse necrosis, and 4=ulceration (transmucosal necrosis).

Statistical significance was determined using Students's t-test for parametric data and the Wilcoxon signed ranks test for non-parametric (morphology) data. All data were reported as the means ± standard érror (SE).

While the foregoing invention has been described in some detail for purposes of clarity and understanding, it will be clear to one skilled in the art from a reading of this disclosure that various changes in form and detail can be made without departing from the true scope of the invention.

What is claimed is:

1. A method of protection of moist stratified squamous epithelia against damage from a noxious luminal substance primarily causing damage by increasing permeability through the paracellular pathway which comprises stabilizing epithelial intercellular junctions in a patient having exhibited the symptoms of gastroesophageal reflux or reflux esophagitis by administering to said patient so as to come into contact with said epithelia an amount sufficient for protecting said epithelia of a sulfonate so as to block the increase in paracellular permeability that occurs with exposure to said noxious luminal substance.

2. The method according to claim 1 wherein said sulfonate is 4-acetamido-4'-isothiocyano-2,2'-stilbene disulfonate, 8-anilinonaphthalene-1-sulfonate, dinitrodisulfonic acid stilbene, sulfonazo III, 4,4'-diisothiocyano-2,2'-stillbene disulfonate, or bromophenol blue.

3. The method according to claim 1 wherein said moist stratified squamous epithelia is esophageal epithelia or buccal epithelia.

4. The method according to claim 1 wherein said noxious luminal substance is acid or N-acetylcysteine.

5. The method of claim 1 wherein said sulfonate is sulfonazo III.

* * * * *

UNITED STATES PATENT AND TRADEMARK OFFICE
CERTIFICATE OF CORRECTION

PATENT NO. : 5,189,056
DATED : February 23, 1993
INVENTOR(S) : Orlando et al.

It is certified that error appears in the above-identified patent and that said Letters Patent is hereby corrected as shown below:

Column 1,
Line 5, insert the following -- This invention was made with federal support under Grant Number 5-R01-DK36013 awarded by the National Institutes of Health. The United States Government has certain rights in the invention. --.

Signed and Sealed this

Fourteenth Day of September, 2004

JON W. DUDAS
*Director of the United States Patent and Trademark Office*